(12) United States Patent
Burr et al.

(10) Patent No.: US 12,042,326 B2
(45) Date of Patent: Jul. 23, 2024

(54) IDENTIFYING ARRANGEMENT ERRORS OF DETECTOR ELEMENTS WITHIN A GAMMA-RAY DETECTOR SYSTEM

(71) Applicant: CANON MEDICAL SYSTEMS CORPORATION, Otawara (JP)

(72) Inventors: Kent C. Burr, Vernon Hill, IL (US); Yi Qiang, Vernon Hill, IL (US); Xiaoli Li, Vernon Hill, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 841 days.

(21) Appl. No.: 17/168,852

(22) Filed: Feb. 5, 2021

(65) Prior Publication Data
US 2022/0252746 A1 Aug. 11, 2022

(51) Int. Cl.
| | |
|---|---|
| A61B 6/03 | (2006.01) |
| A61B 6/42 | (2024.01) |
| A61B 6/58 | (2024.01) |
| G01T 1/29 | (2006.01) |

(52) U.S. Cl.
CPC .......... *A61B 6/58* (2013.01); *A61B 6/037* (2013.01); *A61B 6/4275* (2013.01); *G01T 1/2985* (2013.01)

(58) Field of Classification Search
None
See application file for complete search history.

(56) References Cited

U.S. PATENT DOCUMENTS

| | | | | |
|---|---|---|---|---|
| 8,471,211 B2 * | 6/2013 | Yamada | ............... | G01T 1/1644 |
| | | | | 250/363.01 |
| 9,360,570 B2 * | 6/2016 | Rothfuss | ................ | G01T 1/40 |
| 10,527,741 B2 * | 1/2020 | Cho | ..................... | G01T 1/2985 |
| 10,603,515 B2 * | 3/2020 | Olcott | ................ | A61N 5/1064 |
| 10,698,125 B2 * | 6/2020 | Wang | .................... | G01T 1/2985 |
| 10,775,520 B2 * | 9/2020 | Cho | ....................... | G01T 7/005 |
| 10,914,851 B2 * | 2/2021 | Wang | .................... | G01T 1/2985 |
| 2010/0327168 A1 * | 12/2010 | Yamada | ................ | A61B 6/037 |
| | | | | 250/361 R |
| 2015/0301201 A1 * | 10/2015 | Rothfuss | .............. | G01T 1/1647 |
| | | | | 250/252.1 |
| 2016/0299240 A1 | 10/2016 | Cho et al. | | |

(Continued)

FOREIGN PATENT DOCUMENTS

| | | | | | |
|---|---|---|---|---|---|
| CN | | 107456235 A | | 12/2017 | |
| CN | | 111685785 A * | | 9/2020 | ............. A61B 6/585 |
| WO | WO-2021238929 A1 * | | 12/2021 | ............... A61B 6/58 |

OTHER PUBLICATIONS

Wei. "Intrinsic Radiation in Lutetium Based PET Detector: Advantages and Disadvantages" arXiv: 1501.05372 (Year: 2015).*

(Continued)

*Primary Examiner* — Thomas R Artman
(74) *Attorney, Agent, or Firm* — Oblon, McClelland, Maier & Neustadt, L.L.P.

(57) ABSTRACT

In a gamma-ray detector system, such as a PET detector, coincidence events between multiple detector elements can be caused by inter-detector scattering and/or energy escape of the multi-stage radiation background in the scintillator crystals. Because these types of coincidence events are more likely to happen between nearby elements, they can be measured, analyzed and ultimately used to identify arrangement errors of detector elements in a gamma-ray detector system.

19 Claims, 41 Drawing Sheets

(56) References Cited

U.S. PATENT DOCUMENTS

| | | | |
|---|---|---|---|
| 2017/0276811 A1* | 9/2017 | Wang | G01T 1/2985 |
| 2019/0070437 A1 | 3/2019 | Olcott et al. | |
| 2020/0072988 A1* | 3/2020 | Cho | G01T 7/005 |
| 2020/0363543 A1* | 11/2020 | Wang | G01T 7/005 |
| 2022/0252746 A1* | 8/2022 | Burr | A61B 6/58 |
| 2023/0102139 A1* | 3/2023 | Lyu | G06T 7/0012 |
| | | | 382/131 |

OTHER PUBLICATIONS

Machine translation of CN 111685785 A (Year: 2020).*
Machine translation of WO 2021/238929 A1 (Year: 2021).*

* cited by examiner

FIG. 27

IDENTIFYING ARRANGEMENT ERRORS OF DETECTOR ELEMENTS WITHIN A GAMMA-RAY DETECTOR SYSTEM

FIELD OF THE INVENTION

The methods and systems described herein are directed towards identifying arrangement errors between detector elements in a gamma-ray detector system.

DESCRIPTION OF THE RELATED ART

A gamma-ray detector system, such as a positron emission tomography (PET) scanner, usually includes multiple detector elements such as crystals, modules, and detector units. During manufacture or system service, it is possible that these detector elements may be arranged incorrectly. For instance, detector elements may be inserted in an incorrect orientation or may have swapped cable connections. It is important to verify the actual layout of the detector elements in the system to avoid artifacts in imaging due to incorrect layout.

Often times, the layout is checked by visually inspecting the cable connections and orientation of detector elements, which can be unreliable. Image checks could also be performed, but this method cannot provide immediate error feedback without lengthy calibration procedures or reconstruction. In many cases, if the problem is not detected until the system is fully calibrated, part or all of the lengthy calibration process will have to be repeated, which is time consuming and expensive.

Therefore, in consideration of the above issues, a more efficient approach for identifying arrangement errors between detector elements in a gamma-ray detector system is beneficial.

SUMMARY

To address at least one problem identified with known techniques, the present disclosure describes capturing radiation events within a gamma-ray detector system, and processing the radiation events data to verify the relative positioning and/or identify arrangement errors of detector elements within the detector system.

Inter-detector scattering and background radiation from the scintillator crystals can cause coincidence events. These coincidence events between multiple detector elements can be tracked and processed. Detector elements that are designed to be side-by-side are expected to share more of these coincidence events, whereas detector elements that are designed to be located far from each other are expected to share very few of these coincidence events.

In one embodiment, the average distance between assembly events (coincidence events caused by inter-detector scattering and background radiation from the scintillator crystals) for each detector element is measured to determine if an arrangement error exists. In another embodiment, another distance metric could be used, such as median distance, mode distance, etc.

In another embodiment, the relative correlation between assembly events for each detector element is measured to determine arrangement errors.

Arrangement errors for different detector elements can be identified, such as errors between crystals, modules or detector units.

Additionally, techniques to remove noise and/or bias caused from random assembly events (similar to but slightly different than random coincidence events; see detailed description for more detail) are disclosed.

Further, in another embodiment, a machine learning system and/or look up tables (LUTs) can be incorporated to specifically identify the type of layout error and correct it.

This summary section does not specify every embodiment and/or incrementally novel aspect of the present disclosure or claimed invention. Instead, this summary only provides a preliminary discussion of different embodiments and corresponding points of novelty. For additional details and/or possible perspectives of the invention and embodiments, the reader is directed to the Detailed Description section and corresponding figures of the present disclosure as further discussed below.

BRIEF DESCRIPTION OF THE DRAWINGS

The application will be better understood in light of the description which is given in a non-limiting manner, accompanied by the attached drawings in which:

FIG. 27 shows an example of 10 detector elements that are arranged correctly;

DETAILED DESCRIPTION

Figure 1:
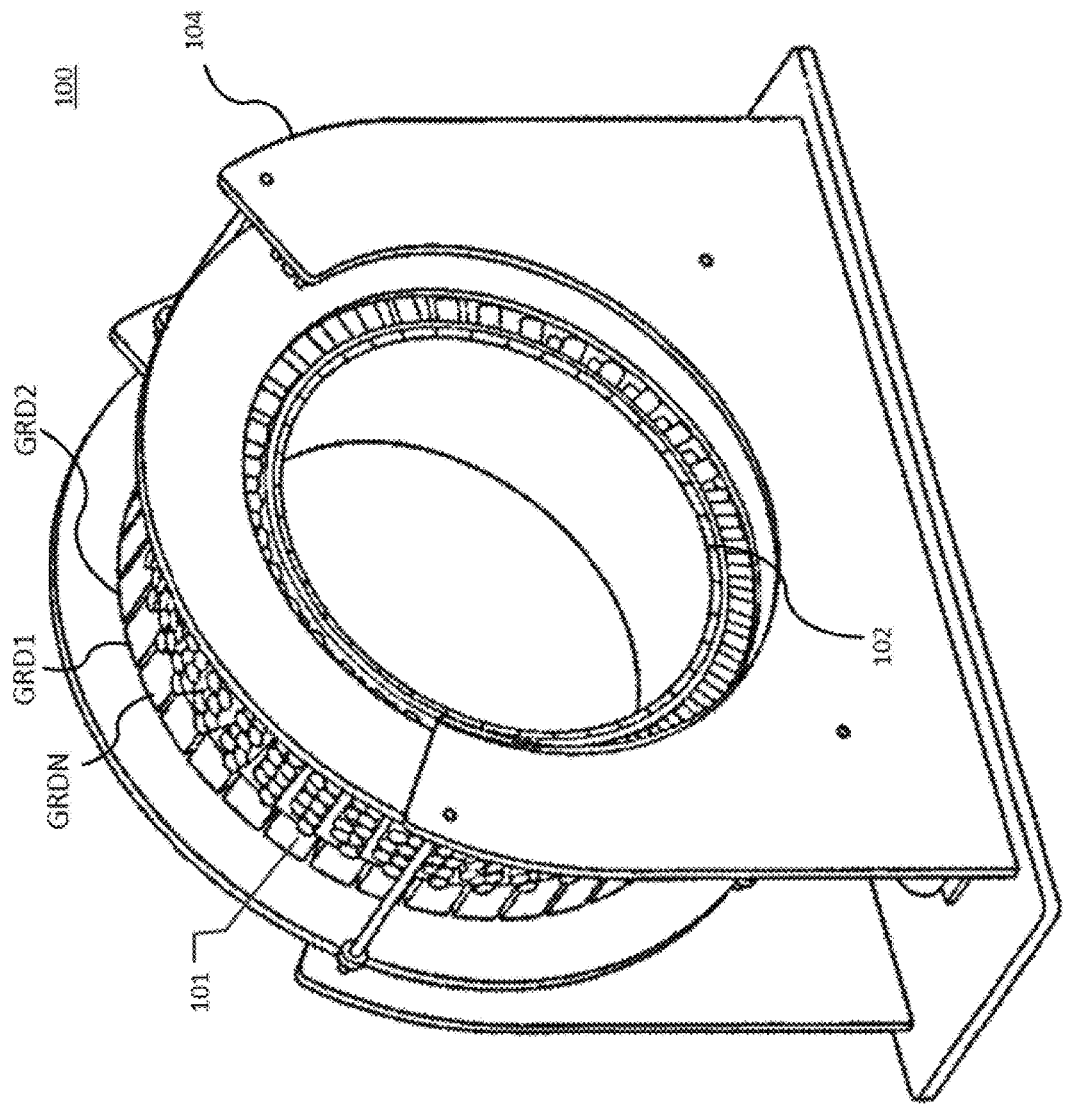
FIG. 1 is an illustration of a perspective view of a positron emission tomography (PET) scanner.

The following disclosure provides many different embodiments, or examples, for implementing different features of the provided subject matter. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The order of discussion of the different steps as described herein has been presented for the sake of clarity. In general, these steps can be performed in any suitable order. Additionally, although each of the different features, techniques, configurations, etc. herein may be discussed in different places of this disclosure, it is intended that each of the concepts can be executed independently of each other or in combination with each other. Accordingly, the present invention can be embodied and viewed in many different ways. This disclosure describes a PET detector system comprising scintillator crystals, photosensors and associated electronics to illustrate the various embodiments, but these concepts can be applied to similar ionizing radiation detector systems, such as gamma-ray and x-ray detectors. Examples of other systems to which this disclosure could be applied include direct conversion semiconductor detectors using materials such as cadmium telluride, cadmium zinc telluride, silicon, and germanium.

Figure 2:
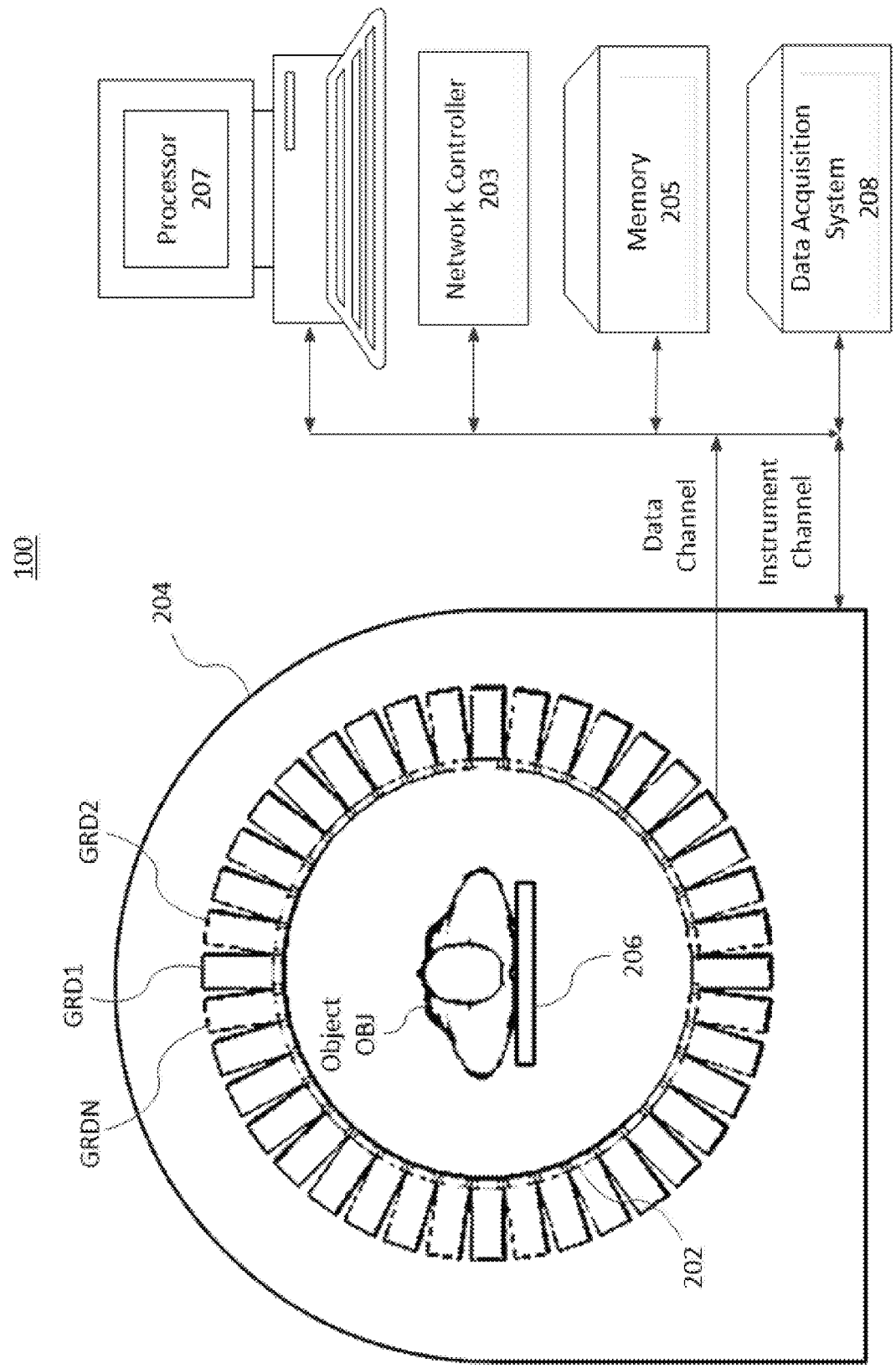
FIG. 2 is a schematic of a PET scanner and associated hardware, according to an exemplary embodiment of the present disclosure.

It can be appreciated that the methods of the present disclosure may be implemented within a PET scanner, as shown in FIG. 1 and FIG. 2. Therefore, FIG. 1 and FIG. 2 show a PET scanner 100 including a number of gamma-ray detectors (GRDs) 101 (e.g., GRD1, GRD2, through GRDN) that are each configured as rectangular detector modules. According to one implementation, each PET detector ring, which forms a circular bore 102 about a gantry 104, includes 40 GRDs. In another implementation, there are 48 GRDs, the higher number of GRDs being used to create a larger bore size for the PET scanner 100. The GRDs include scintillator crystal arrays for converting the gamma rays into scintillation photons (e.g., at optical, infrared, and ultraviolet wavelengths), which are detected by photodetectors. Each GRD can include a two-dimensional array of individual detector crystals, which absorb gamma radiation and emit scintillation photons. The scintillation photons can be detected by a two-dimensional array of photomultiplier tubes (PMTs) that are also arranged in the GRD. A light guide can be disposed between the array of detector crystals and the PMTs. Further, each GRD can include a number of PMTs of various sizes, each of which is arranged to receive scintillation photons from a plurality of detector crystals. Each PMT can produce an analog signal that indicates when scintillation events occur, and an energy of the gamma ray producing the detection event. Moreover, the photons emitted from one detector crystal can be detected by more than one PMT, and, based on the analog signal produced at each PMT, the detector crystal corresponding to the detection event can be determined using Anger logic and crystal decoding, for example. However, Anger arithmetic is not necessarily required when there is a one-to-one correspondence between the crystals and the photodetectors. For detectors with one-to-one correspondence between crystals and photodetectors, silicon photomultipliers (SiPMs) or avalanche photodiodes (APDs) are common choices for the photo detectors.

FIG. 2 shows a schematic view of a PET scanner system having GRDs arranged to detect gamma-rays emitted from an object OBJ. The GRDs can measure the timing, position, and energy corresponding to each detected gamma-ray. In one implementation, the gamma-ray detectors are arranged in a PET detector ring, as shown in FIG. 1 and FIG. 2, and as described herein. It can be appreciated that the single PET detector ring of FIG. 2 can be extrapolated to include any number of PET detector rings along an axial length of the PET scanner. The detector crystals can be scintillator crystals, which have individual scintillator elements arranged in a two-dimensional array and the scintillator elements can be any known scintillating material (e.g., LYSO, BGO, LSO). The PMTs can be arranged such that light from each scintillator element is detected by multiple PMTs to enable Anger arithmetic and crystal decoding of scintillation events.

FIG. 2 shows an example of the arrangement of the PET scanner 100, in which the object OBJ to be imaged rests on a table 206 and the GRD modules GRD1 through GRDN are arranged circumferentially around the object OBJ and the table 206. The GRDs may comprise a PET detector ring and may be fixedly-connected to a circular bore 202 that is fixedly-connected to a gantry 204. The gantry 204 houses many parts of the PET scanner. The gantry 204 of the PET scanner also includes an open aperture, defined by the cylindrical bore 202, through which the object OBJ and the table 206 can pass, and gamma-rays emitted in opposite directions from the object OBJ due to an annihilation event can be detected by the GRDs and timing and energy information can be used to determine coincidences for gamma-ray pairs.

In FIG. 2, circuitry and hardware is also shown for acquiring, storing, processing, and distributing gamma-ray detection data. The circuitry and hardware include a processor 207, a network controller 203, a memory 205, and a data acquisition system (DAS) 208. The PET imager also includes a data channel that routes detection measurement results from the GRDs to the DAS 208, the processor 207, the memory 205, and the network controller 203. The data acquisition system 208 can control the acquisition, digitization, and routing of the detection data from the detectors. In one implementation, the DAS 208 controls the movement of the table 206. The processor 207 performs functions including identifying arrangement errors, pre-reconstruction processing of the detection data, image reconstruction, and post-reconstruction processing of the image data.

According to an embodiment, the processor 207 of the PET scanner 100 of FIG. 1 and FIG. 2 can be configured to perform the methods as described herein. The processor 207 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 305 can be a hard disk drive, CD-ROM drive, DVD drive, FLASH drive, RAM, ROM or any other electronic storage known in the art. The memory 205 may be non-volatile, such as ROM, EPROM, EEPROM or FLASH memory. The memory 205 can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 207 can execute a computer program including a set of computer-readable instructions that perform methods described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the PET scanner may include a display for displaying a reconstructed image and the like. The display can be an LCD display, CRT display, plasma display, OLED, LED or any other display known in the art.

The network controller 203, such as an Intel Ethernet PRO network interface card from Intel Corporation of America, can interface between the various parts of the PET imager. Additionally, the network controller 203 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

Figure 3:
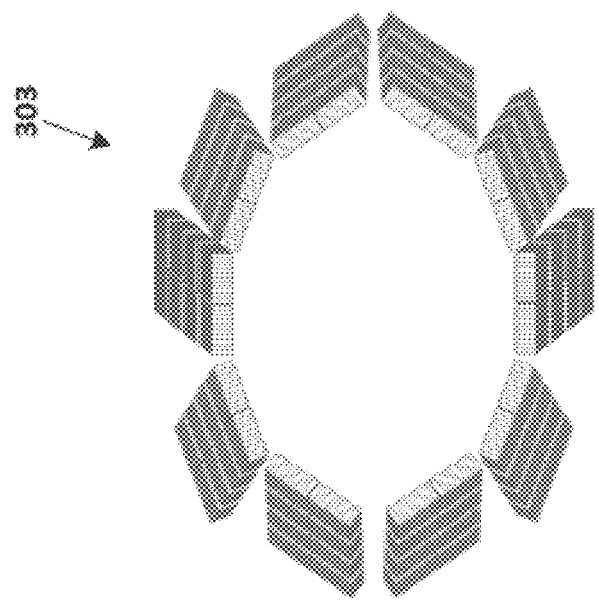
FIG. 3 shows crystals, modules, detector units and a detector ring in relation to one another.
Figure 3:
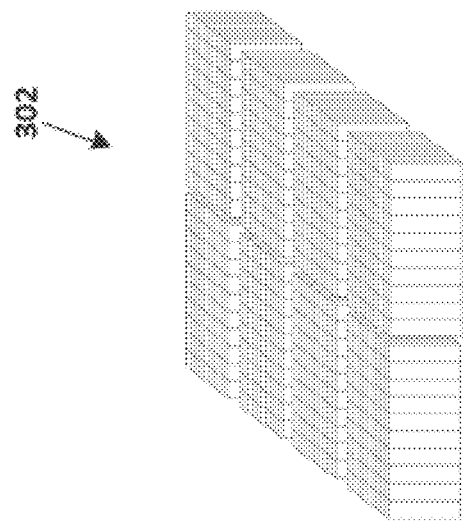
Figure 3:
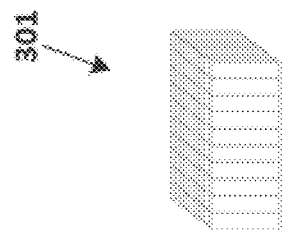

FIG. 3 highlights a subset of components within a PET scanner 100 that will be commonly referenced in this disclosure. A module 301 may generally be the smallest element which is able to operate independently as a PET detector, and comprises scintillator crystals and photosensors (and optional electronics). For example, the module 301 in FIG. 3 includes of an array of crystals. A detector unit 302 may be composed of a plurality of modules 301. For example, the detector unit 302 in FIG. 3 is made up of eight modules 301. A detector ring 303 may be composed of a plurality of detector units 302. For example, the detector ring 303 in FIG. 3 includes 10 detector units. The detector ring forms the circular bore 102 about the gantry 104, as previously mentioned in FIG. 1. Herein, a detector element can be defined as a crystal, module 301 or a detector unit 302.

Detector elements, which are electrically and/or optically independent, can often form coincidence events due to inter-detector scattering or energy escape of the multi-stage background radiation in the crystal. These multi-detector events between detector elements (i.e. between crystals, between modules, between detector units) can be used to verify the relative positioning of detector elements and detect errors in layout.

Figure 4:
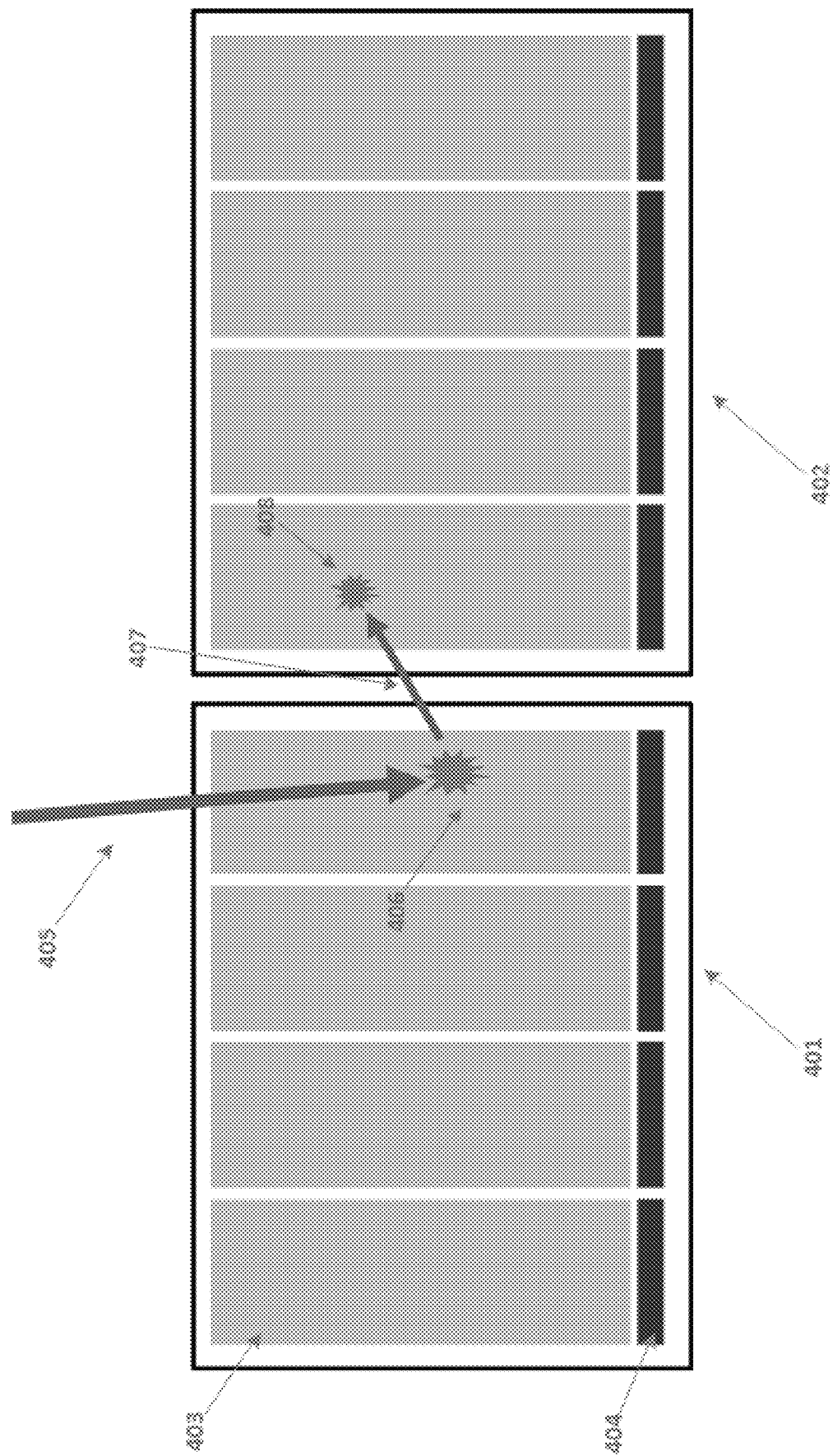
FIG. 4 illustrates an example of a coincidence event caused by inter-detector scattering.

An example of inter-detector scattering is shown in FIG. 4. Shown are a first detector module 401 and second detector module 402, each comprising crystals 403 and photo sensors 404. An external source of high-energy gamma ray 405 (such as Cs-137 (662 keV) or Ge-68 (coincident 511 keV pairs) enters into one of the crystals 403 in the first module 401 and causes a first energy deposition 406 (i.e. a hit). A Compton-scattered gamma ray 407 causes a second hit 408 in the second detector module 402. The first hit 406 and second hit 408 occur nearly simultaneously in the two different detector elements. This inter-detector scattering can form coincidence events between two or more detector elements.

Figure 5:
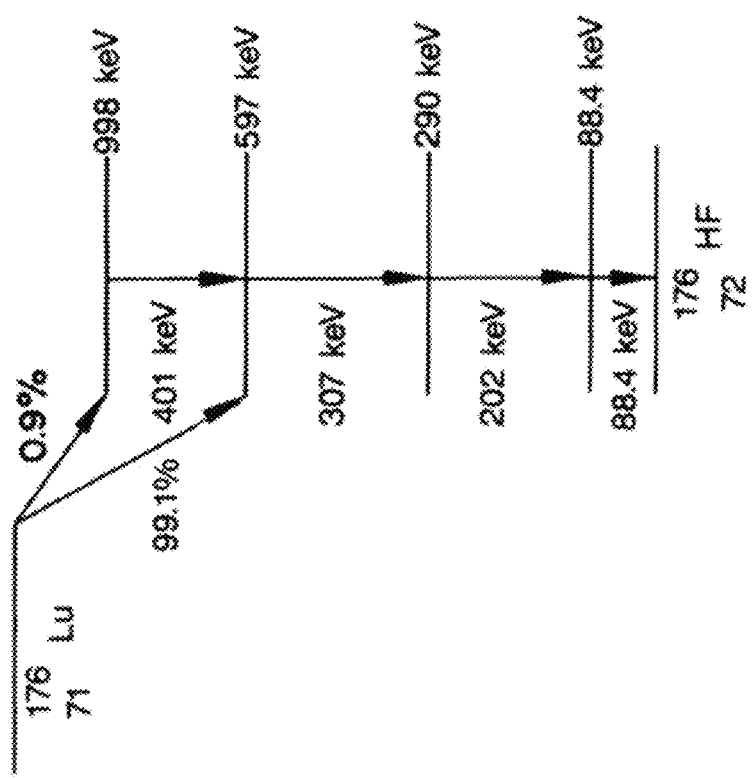
FIG. 5 shows the decay of Lu-176 by beta-emission followed by a cascade of gamma rays.
Figure 6:
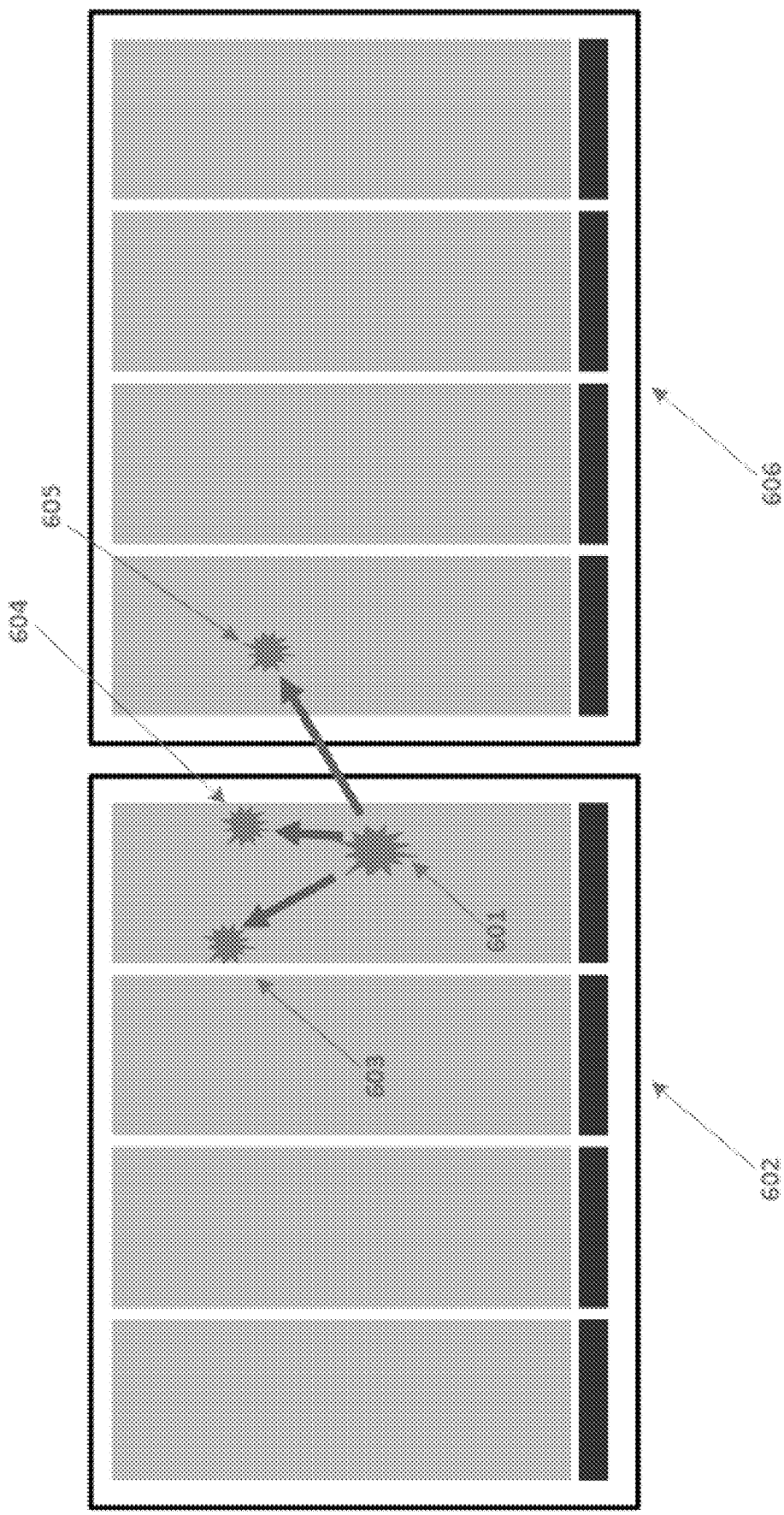
FIG. 6 illustrates an example of a coincidence event caused by the background radiation in a crystal.

Additionally, some scintillator materials are radioactive (i.e. the scintillator crystal produces background/intrinsic radiation). For example, in LYSO or LSO (two common PET scintillators), Lu-176 is naturally present. As shown in FIG. 5, Lu-176 decays by a beta-emission followed by a nearly simultaneous cascade of gamma rays. The energy from the beta emission is usually contained in the element in which the decay occurred, but the gamma rays sometimes may be absorbed in other detector elements. This type of background radiation in the crystal can also cause coincidence events. For example, FIG. 6 illustrates Lu-176 decay 601 in the first detector module 602. The decay 601 causes a 202 keV energy deposition 603 in the first module 602, a 88 keV energy deposition 604 in the first module 602, and a 307 keV energy deposition 605 in the second detector module 606. It can be appreciated that the energy can be deposited in two detector elements nearly simultaneously, which can form a coincidence event.

Because these types of coincident events normally happen between detector elements that are close to each other compared to detector elements that are farther apart, these coincidence events can be tracked, measured and compared to a threshold or designed layout to estimate arrangement errors.

Figure 7A:
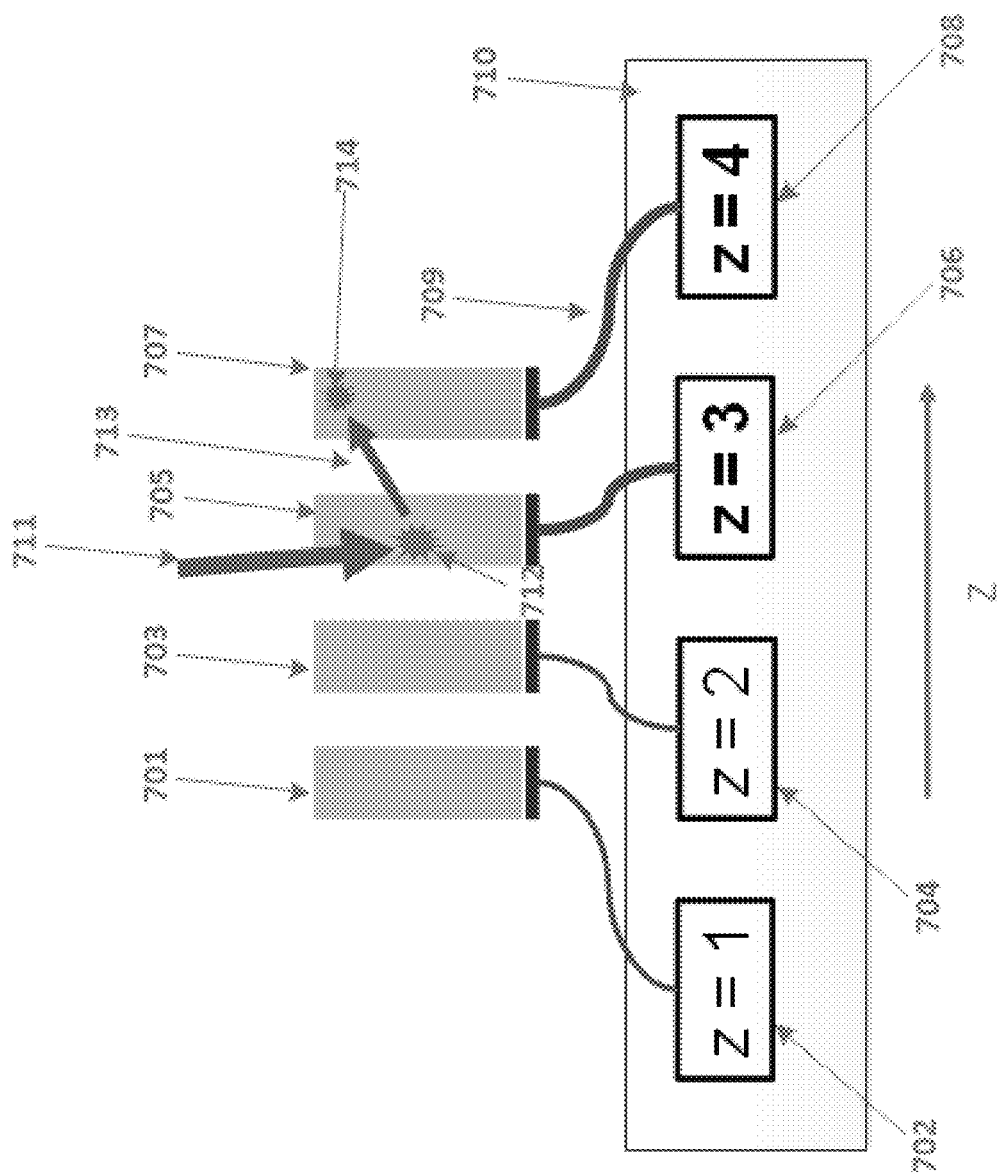
FIG. 7A illustrates an example of an expected layout between detector elements.
Figure 7B:
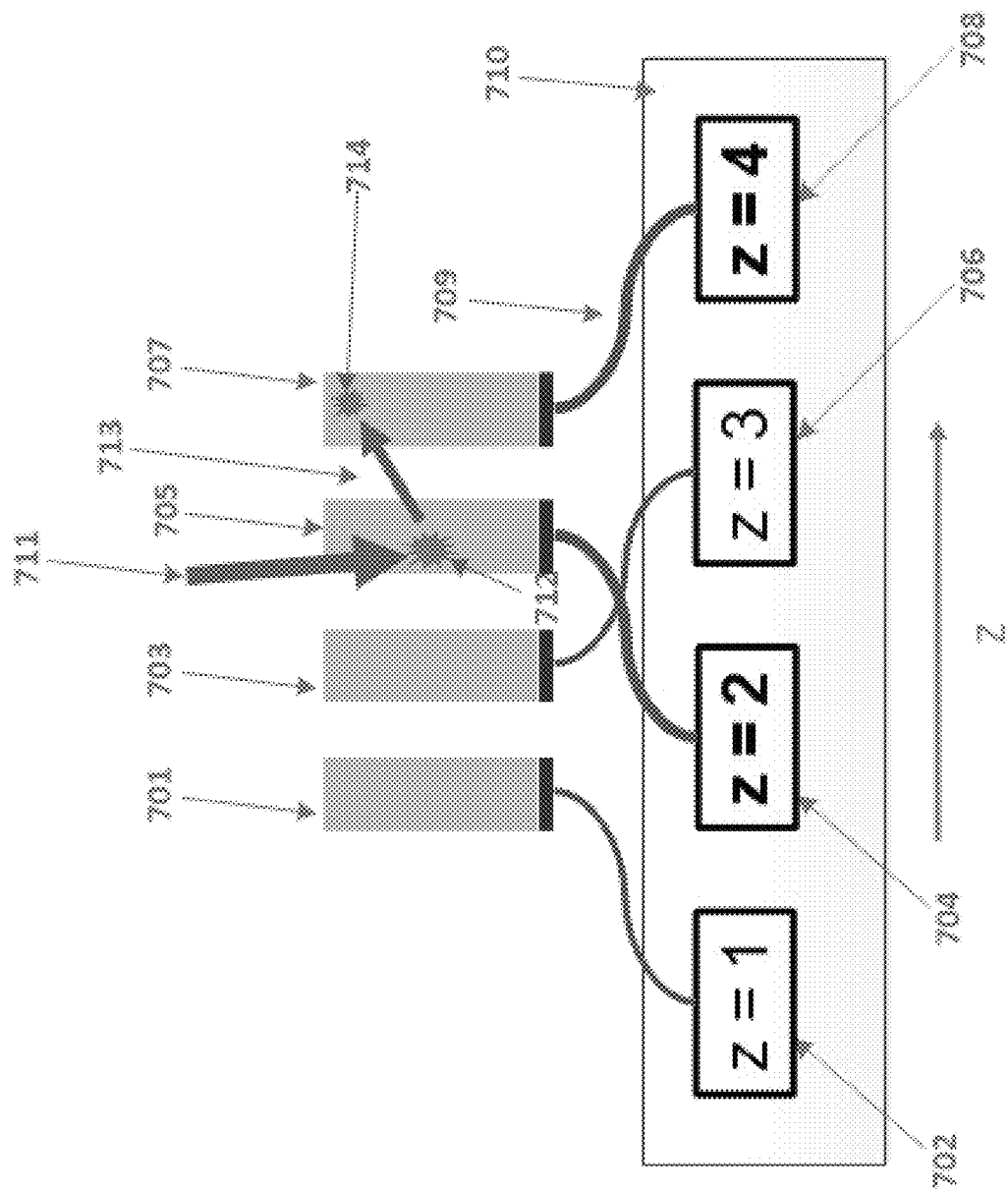
FIG. 7B illustrates an example of a measured layout between detector elements.

As an example and introduction to the concept, FIG. 7A and FIG. 7B illustrate an embodiment of the present disclosure where the layout error is a cable connection error (misconnected modules). A designed/expected layout is shown in FIG. 7A. Module A 701 is connected to Channel 1 702, Module B 703 is connected to Channel 2 704, Module C 705 is connected to Channel 3 706, and Module D 707 is connected to Channel 4 708. Each module is connected via cable 709 to its respective channel, and the channels are part of a data acquisition system 710. In the example, a high energy incident gamma ray 711 may cause a first hit 712 in Module C 705 and a Compton-scattered gamma ray 713 may cause a second hit 714 in Module D 707. The first hit 712 is registered by Channel 3 706, and the second hit 714 is registered by Channel 4 708. The resulting data can be processed and a distance between hits can be determined to be, for instance, one (i.e. |4−3|=1). This result might be typically expected as Module C 705 and Module D 707 are adjacent. A measured/realized layout is shown in FIG. 7B. Again, each module is connected to a channel via cable and the channels are part of the data acquisition system. In this instance, however, two cables are swapped, as Module A 701 is connected to Channel 1 702, Module B 703 is connected to Channel 3 706, Module C 705 is connected to Channel 2 704, and Module D 707 is connected to Channel 4 708. Again, a high energy incident gamma ray 511 may cause a first hit 712 in Module C 705 and a Compton-scattered gamma ray 713 may cause a second hit 714 in Module D 707. As the cables are incorrectly connected, however, the first hit 712 is registered by Channel 2 704, and the second hit 714 is registered by Channel 4 708. The resulting data can be processed and a distance between hits can be incorrectly determined to be, for instance, two (i.e. |4−2|=2). In an embodiment wherein a predetermined threshold is established, the error can be identified (e.g. by a processor) and proper adjustments/corrections can be made. Adjustments and corrections might include manual swapping of the incorrectly connected cables or adjusting one or more look up tables (LUTs) used to relate each detector element to its physical location. In the present exemplary embodiment, only a single event was considered in identifying a defect. In another exemplary embodiment, a defect is identified after processing many events so as to minimize the effect of random statistical fluctuations.

Figure 8:
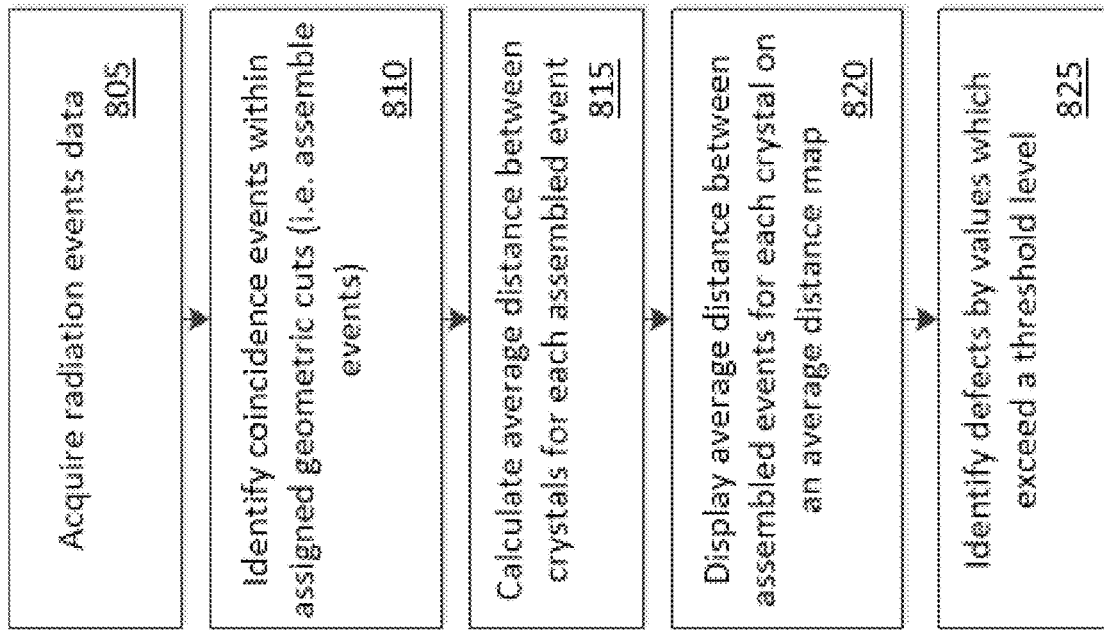
FIG. 8 is flowchart walking through one exemplary embodiment for detecting arrangement errors.

The preceding concepts can be applied in many different embodiments. The flowchart of FIG. 8 outlines an exemplary embodiment of the present disclosure. Initially, radiation events data (i.e. the hits) can be acquired at step 805. The captured radiation events data can include position information (e.g. location of detector element where the hit occurred), time of each hit, and amount of energy deposited by each hit.

At step 810, the acquired radiation events data can be used to form coincidence events between detector elements. Coincidence events can be formed either in real-time through coincidence circuitry or offline through comparison of time measurements in software. Coincidence events, in the context of a traditional PET scan, typically refer to the events that originated as a result of positron annihilation along a line of response (LOR) between two detectors. Coincidence events, as described in the present disclosure, focus predominantly on coincidence events caused by inter-detector scattering or energy escape of multi-stage background radiation in the scintillator crystals. To this end, the coincidence events that are identified are events caused by inter-detector scattering and/or background radiation. Under normal operation, the coincidence events caused by inter-detector scattering or energy escape of the multi-stage background radiation in the scintillator crystals are more likely to occur in nearby detector elements (rather than detector elements on opposite ends of a LOR), and the frequency of these coincidence events usually decreases as a distance between the detector elements becomes larger. In order to differentiate between these specific coincidence events and the traditional coincidence events that typically happen between detectors along a LOR, geometric constraints (i.e. geometric cuts defining sub-regions) may be applied to the detector ring. In this way, hits that occur between multiple detector elements within a coincidence time window and within their respective geometrical constraints (i.e. sub-regions) can be identified as, or referred to as, an assembly event. The process of collecting the assembly events is referred to as assembling the events.

Figure 9:
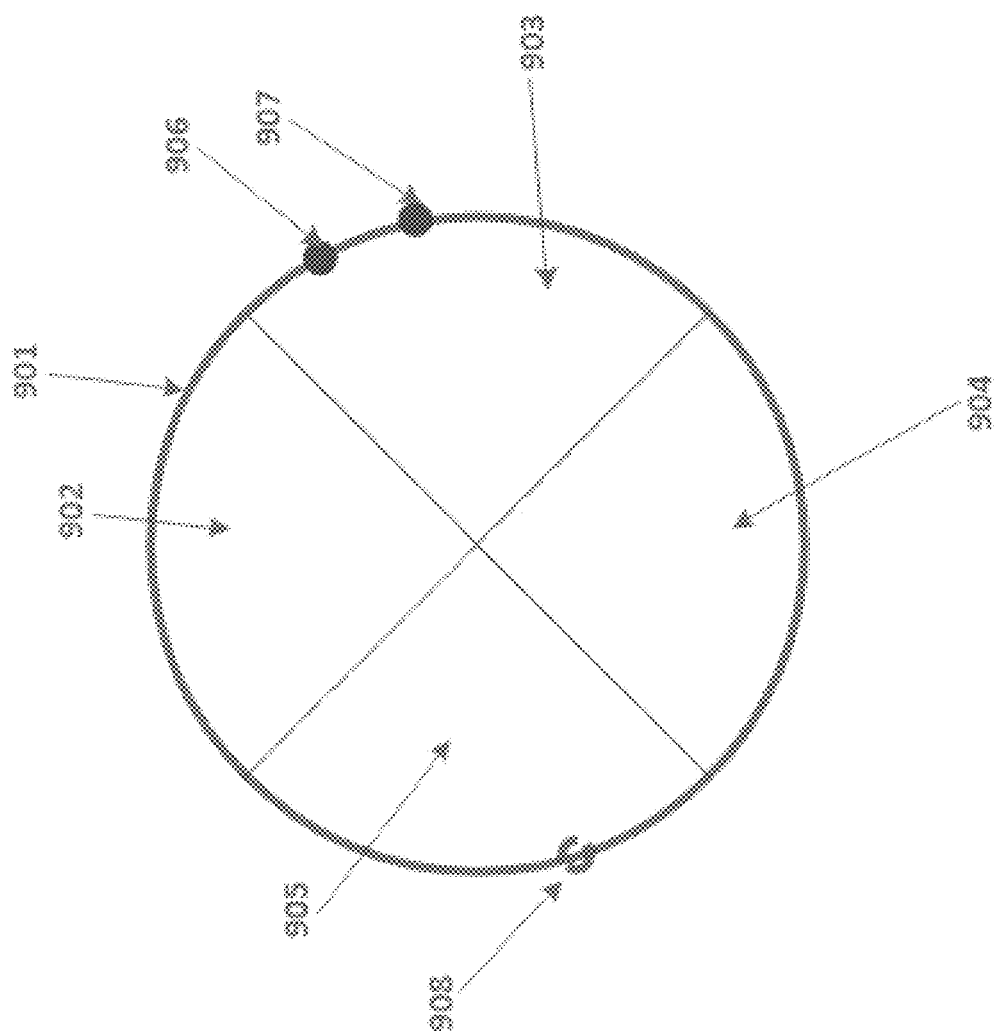
FIG. 9 illustrates an example of an assembly event created by using fixed sub-regions within the detector ring.

According to an embodiment, a geometric cut can divide the detector ring into fixed sub-regions. For example, as shown in FIG. 9, the detector ring 901 could be divided into a first quadrant 902, a second quadrant 903, a third quadrant 904, and a fourth quadrant 905. Hit A 906, Hit B 907, and Hit C 908 may all occur within a coincidence window (Δt), but only Hit A 906 and Hit B 907 would be assembled into an assembly event as they were in the same quadrant 903. Hit C 908, therefore, is not assembled into an assembly event with Hit A 906 and Hit B 907 because it occurred outside the sub-region region defined by the geometric cut. Only coincidence events that happened within each respective sub-region would be assembled into an assembly event. The fixed sub-regions defined by the geometric cut could all be of equal size, or the various sub-regions could be varying sizes.

Figure 10:
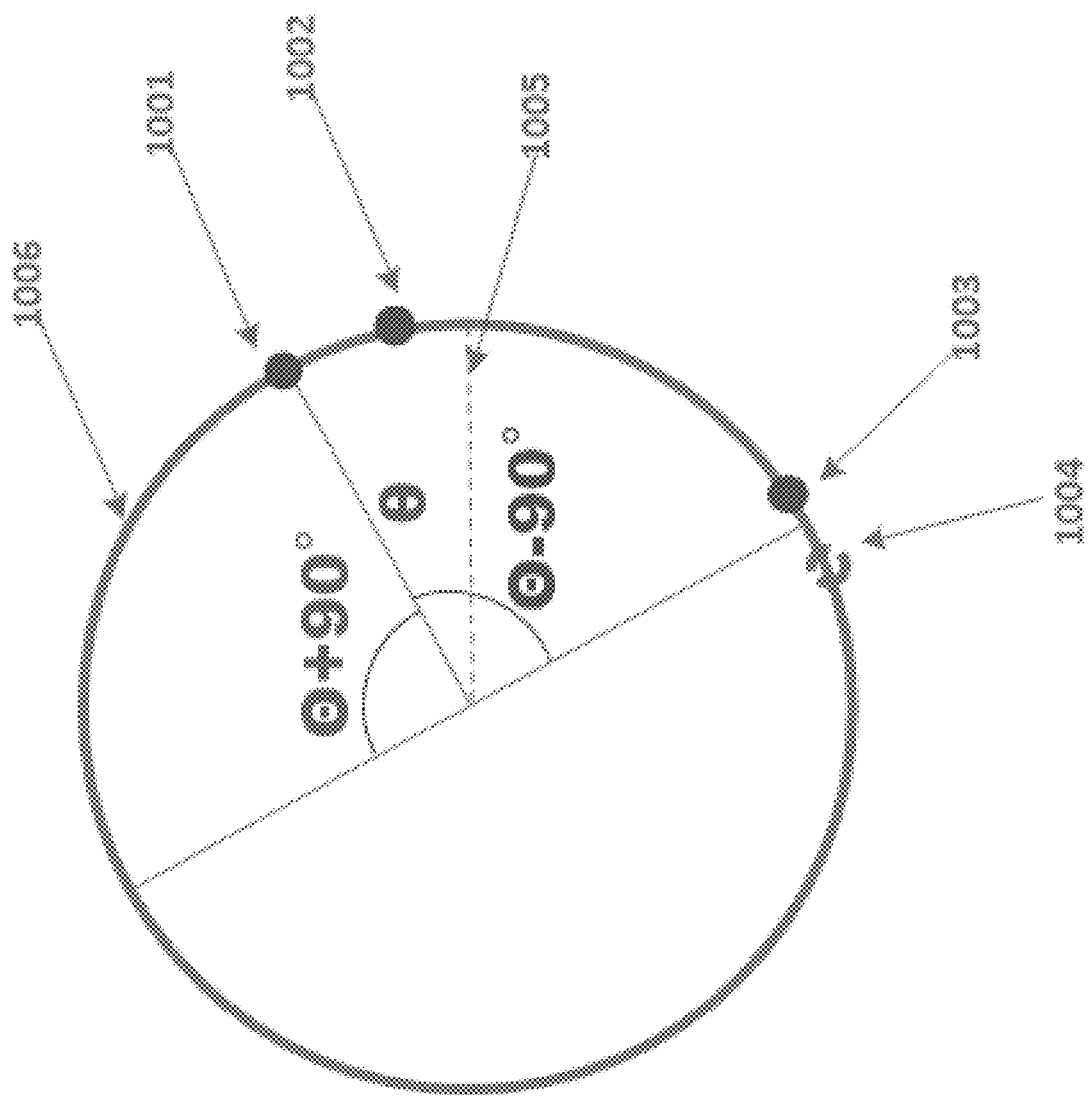
FIG. 10 illustrates an example of an assembly event created by centering the geometric sub-region on the hit with the largest energy.

FIG. 10 shows an example of a geometric constraint that may be employed, according to an exemplary embodiment of the present disclosure. For each identified coincidence event, the geometric region could be centered on an individual event having a maximum energy of each event within a group of hits within the coincidence window. Hit A 1001, Hit B 1002, Hit C 1003, and Hit D 1004, for instance, may be detected within a predetermined coincidence time window. Of the four hits, Hit A 1001 may have the maximal energy. If Hit A 1001 occurred at an angle θ from the zero degree reference point 1005 in the detector ring 1006, all hits within 90 degrees of θ could be assembled into an assembly event including Hit A 1001. In this instance, the assembly event would include Hit B 1002 and Hit C 1003. Hit D 1004 would not be included in the assembled event because it did not occur within θ+/−90 degrees of Hit A 1001. Of course, other tolerances in addition to 90 degrees can be used in different embodiments, as appropriate.

Returning now to FIG. 8, an average distance between all the assembled events that occurred for each detector element (in this case, the scintillator crystals) can be calculated at step 815. In other embodiments, a different metric may be used, such as a median distance or a mode distance, for instance, and a different detector element may be used to calculate the distance between detector elements (e.g. between modules or between detector units).

To elaborate on the latter point, the hits could be detected at different levels of the detector elements: (1) the crystal/pixel level, (2) the module level, or (3) the detector unit level. The crystal/pixel level is the lowest level, followed by the module level, and then the detector unit level. Other levels may be defined, as appropriate. Each of these levels refers to a detector element that is used in a position calculation. As an example, if an average distance between detector elements is calculated at the crystal level, then the position of each crystal is used in a position calculation. Alternatively, if an average distance is calculated at the module level or detector unit level, then only the positions of the module or detector unit (respectively) would be used in a position calculation. This concept of levels can also be applied when calculating a correlation between detector elements, which will be described in greater detail with reference to subsequent Figures.

In an embodiment, any level of calculation will be able to detect positioning or cabling errors at that same level. For example, if the calculation is performed on the module level, swapped modules could be detected. A lower level can also detect positioning or cabling errors at levels above it. For example, swapped modules within the same detector unit could also be detected at the crystal level, but not at the detector unit level.

In order to be sensitive to a rotation of a detector element, calculations must be performed on a level lower than the rotated detector element. For example, to be able to detect rotation errors of modules, the calculations must be performed on a lower level, which, in this instance, would be the crystal level. Similarly, in order to detect rotations on the detector unit level, calculations must be performed on the module or crystal level.

Returning again to FIG. 8, an average distance between assembly events for each detector element (in this example, between crystals) can be displayed on an average distance map at step 820. The collected distance metric data (in this case the average distance between assembly events) can be displayed on a map to aid in visualization of the collected results. It can be appreciated that step 820, as described above, is optional and can be omitted in other embodiments without impacting function of the method.

Figure 11A:
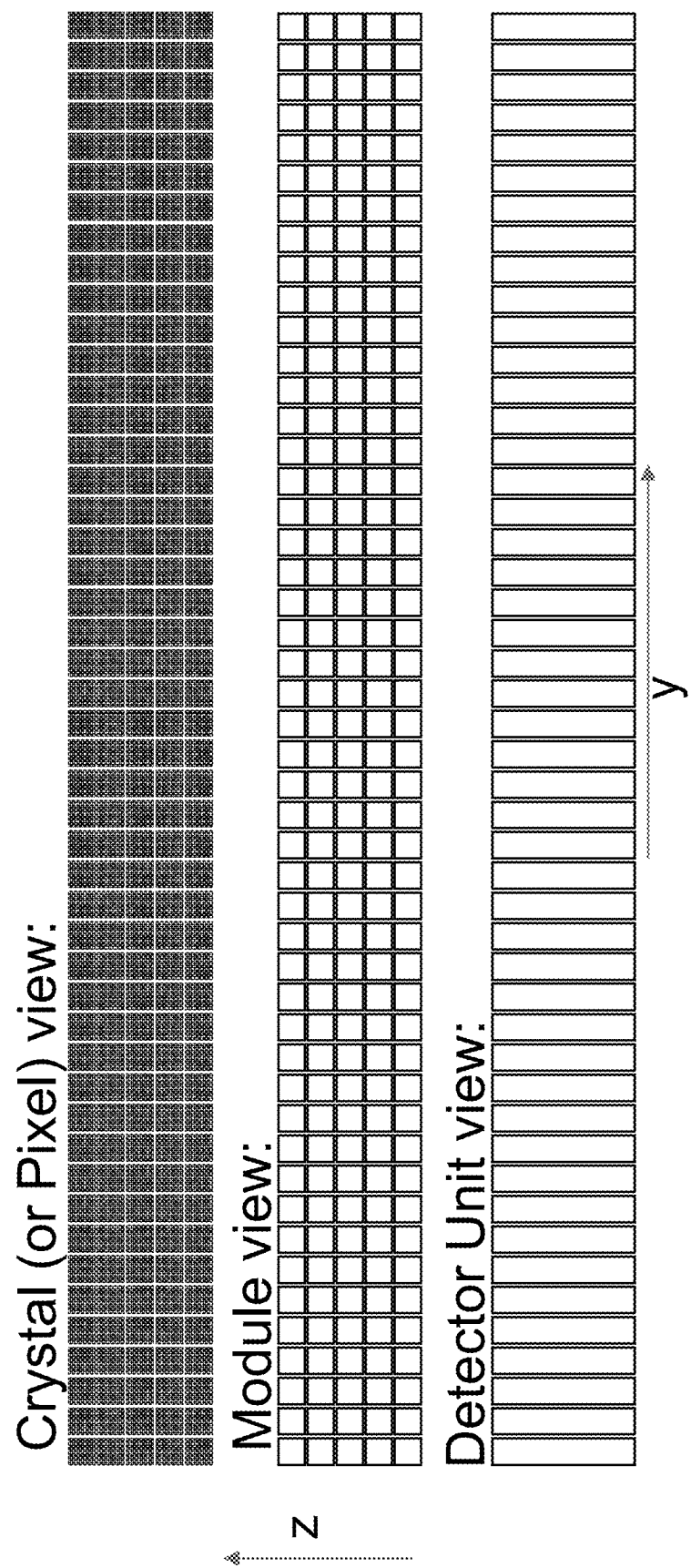
FIG. 11A shows an example of an unwrapped, two-dimensional detector ring in the crystal (or pixel) view, module view, and detector unit view.
Figure 11B:
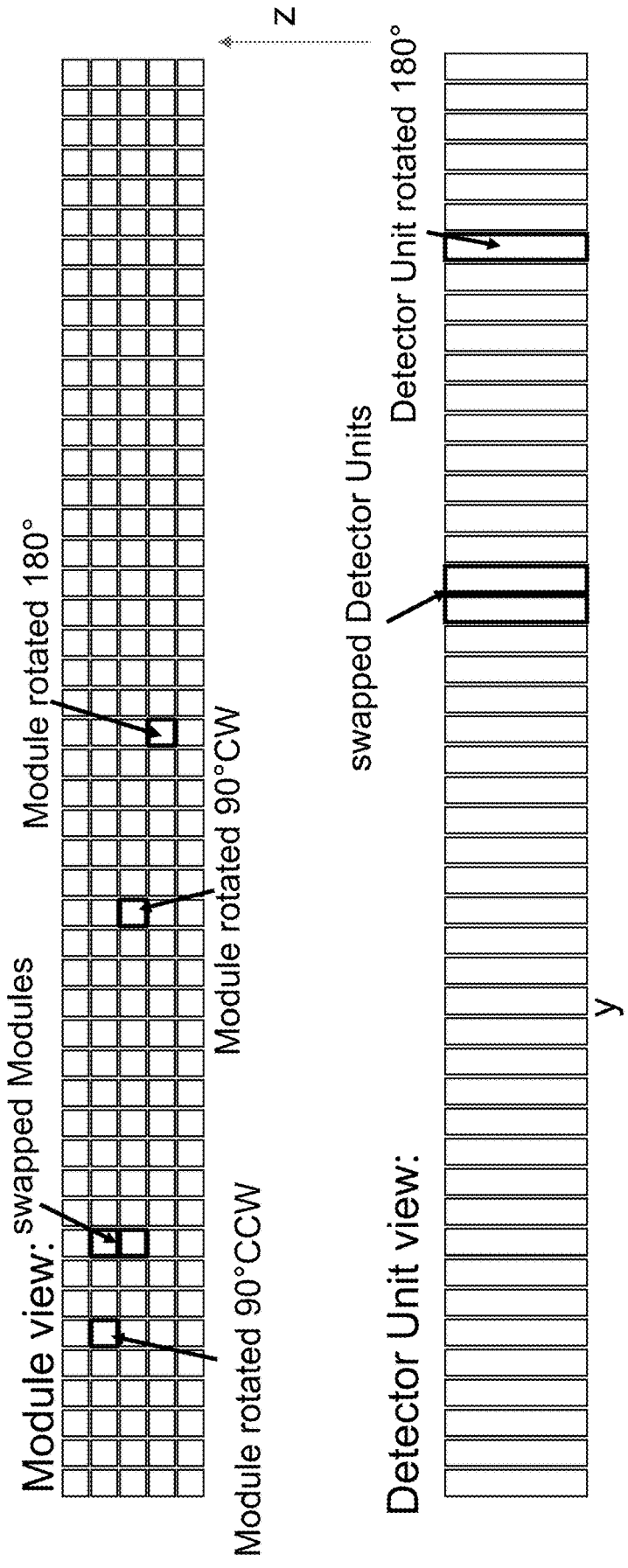
FIG. 11B illustrates various arrangement errors that were created on the detector system.
Figure 11C:
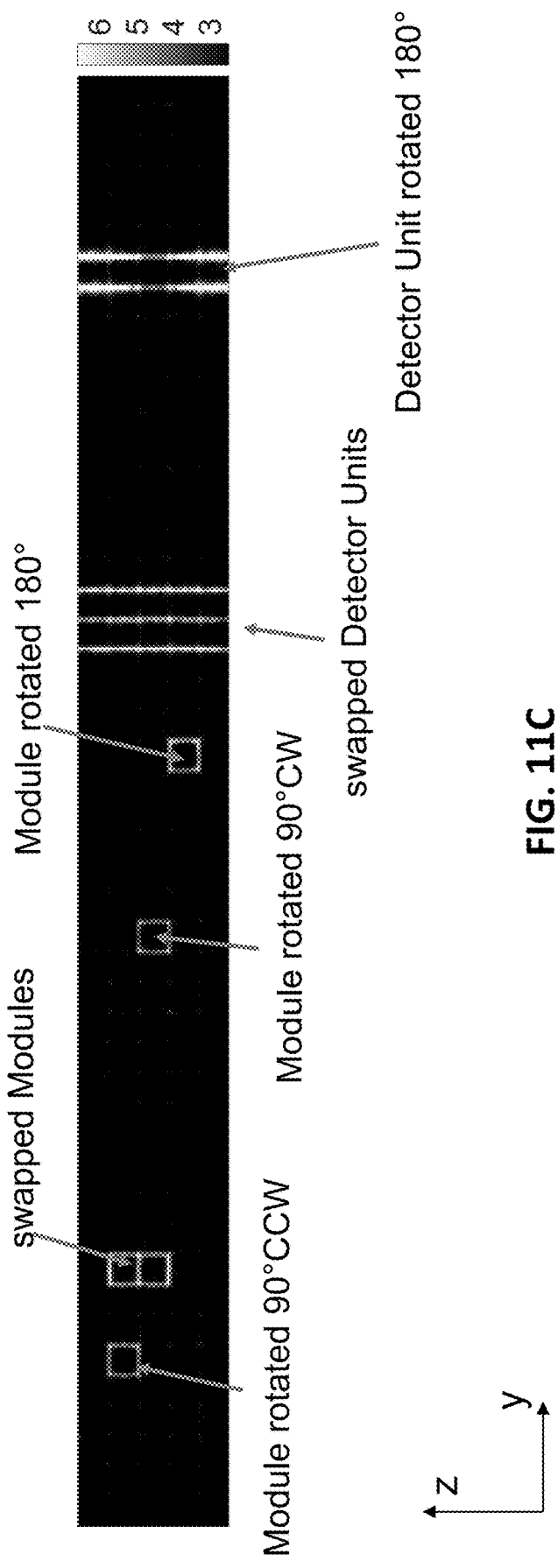
FIG. 11C is an example of an average distance map at the crystal/pixel level.
Figure 11D:
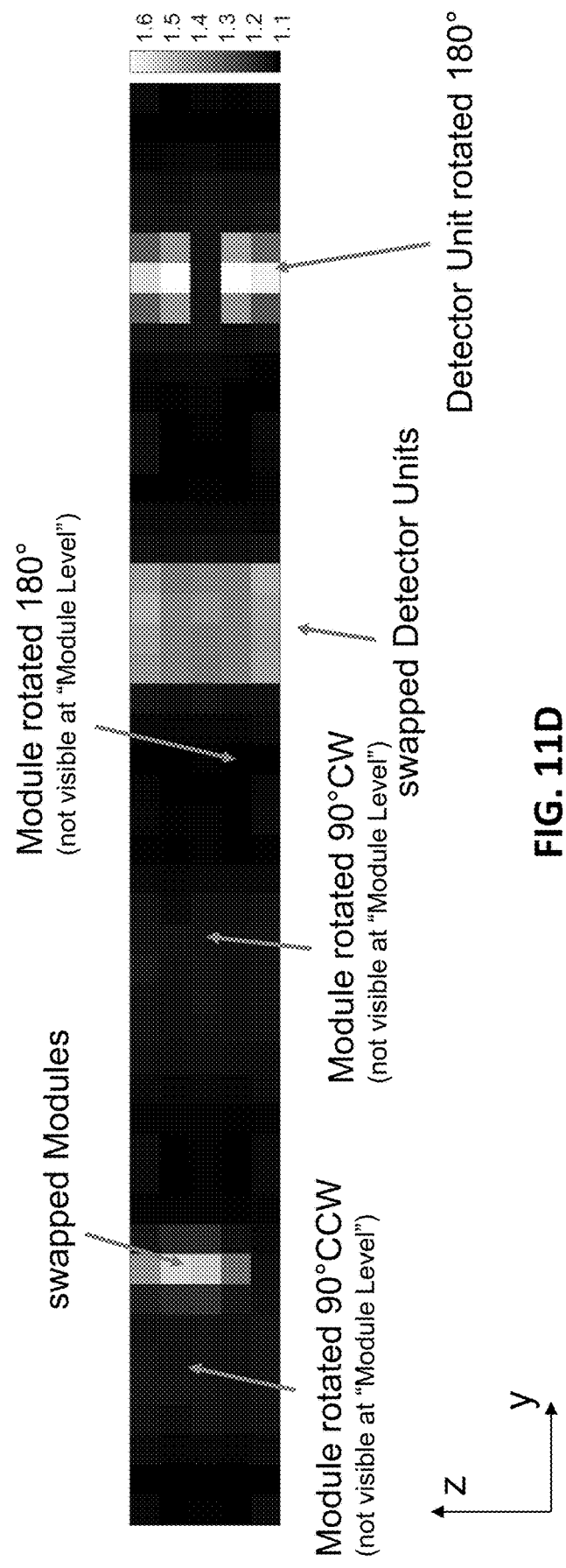
FIG. 11D is an example of an average distance map at the module level.
Figure 11E:
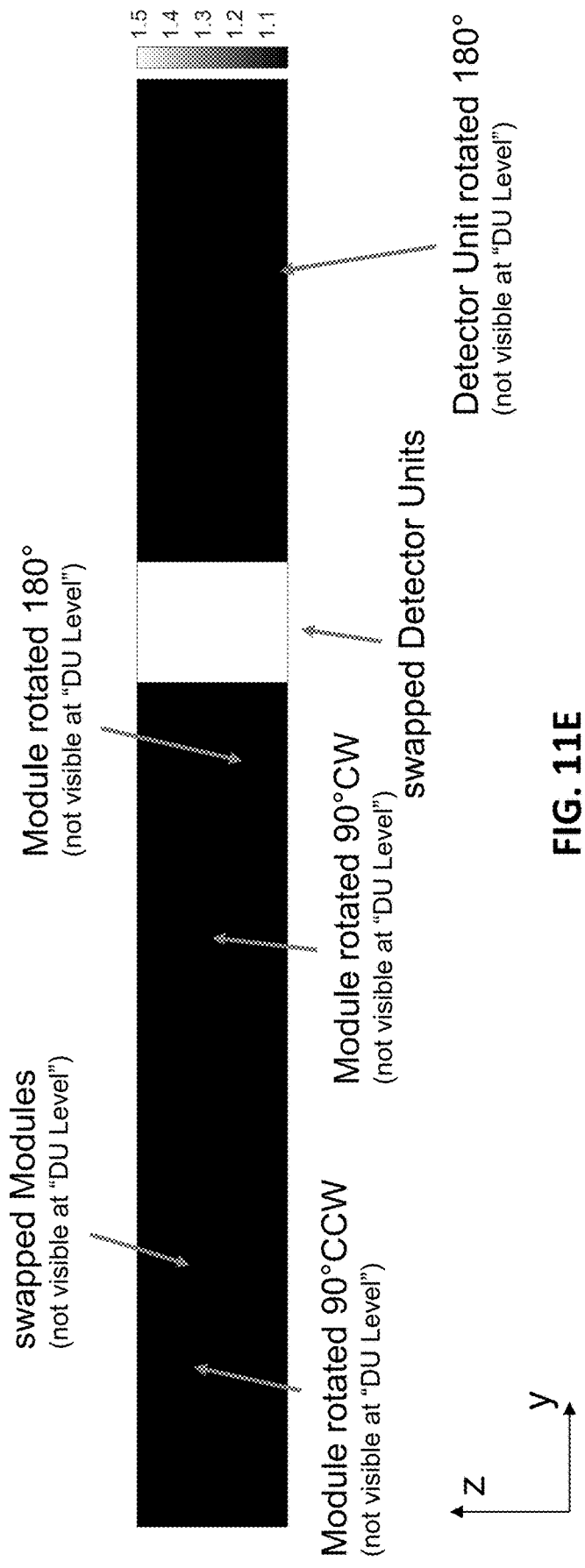
FIG. 11E is an example of an average distance map at the detector unit level, respectively.

To this end, FIG. 11A shows an unwrapped, two-dimensional detector ring with views at three different levels. There is a crystal (or pixel) level view, a module level view, and a detector unit view. As shown in FIG. 11A, the detector ring can include 48 detector units, wherein each detector unit includes 5×1 modules and each module includes 12×12 crystals. FIG. 11B shows various arrangement errors that were intentionally created to the detector ring, and FIG. 11C-11E illustrate the captured results at three different levels. FIG. 11C, for instance, shows an average distance map at the crystal level, wherein all defects, indicated here by the detector elements with lighter hues, are visible. FIG. 11D shows the average distance map at the module level, wherein module swaps and detector unit level defects are visible (as indicated here by the detector elements with the lighter hues), but module rotations are not. Moreover, FIG. 11E shows the average distance map at the detector unit level, wherein only detector unit swaps are visible (as indicated by the detector units with lighter hues).

At step 825, defects can be identified by values which exceed a threshold level. For instance, layout errors can be identified through a visual inspection of the collected data (e.g. inspecting the average distance map). The data could also be compared to a predetermined threshold level to identify any errors. In an embodiment, the predetermined threshold level may be set sufficiently low that all defects are identified but high enough that the rate of false positives is low. Noise and bias, for instance, may be determining factors in setting the predetermined threshold level for detecting defects. As an alternative to setting an explicit threshold, at step 825 a trained operator can inspect the image and identify defects based on experience from having viewed many examples of systems with and without defects.

Further to the above, random assembly events are a significant contributor to noise and bias. Before defining a random assembly, however, an understanding of an initiating event must be developed. An initiating event is an event which routinely causes a single hit (i.e. all energy is deposited in a single crystal—the energy might be deposited in separate discrete processes, such as Compton scattering followed by photo-electric absorption, but these are not resolved as separate detection events by the detector if they occur in the same pixel, since they occur nearly simultaneously). A single positron annihilation normally results in two initiating events because the two 511 keV gamma rays emitted from the annihilation will routinely cause two hits, wherein each 511 keV gamma ray will hit different crystals, and each is a separate initiating event. Lu-176 decay within a scintillator crystal in the detector, however, is typically a single initiating event. Even though Lu-176 decay creates a beta particle and a cascade of gamma rays, this decay often creates only a single hit as the beta particle and the cascade of gamma rays are normally absorbed within the scintillator crystal.

Further to the above, while an initiating event often causes only a single hit, a single initiating event may cause multiple hits. For example, as described in FIG. 6, a single Lu-176 decay may result in a portion of energy being deposited within the crystal in which the decay occurred, while another portion of energy is deposited in a neighboring crystal by a gamma ray which escapes from the first crystal. Another case of a single initiating event causing multiple hits is a 511 keV gamma ray Compton scattering in one crystal (and depositing some energy in the process) and the scattered gamma ray depositing its energy in a second crystal (such as explained in FIG. 4). The goal of the assembly process, therefore, is to identify hits which originated from the same initiating event (i.e. assemble the events).

Figure 12:
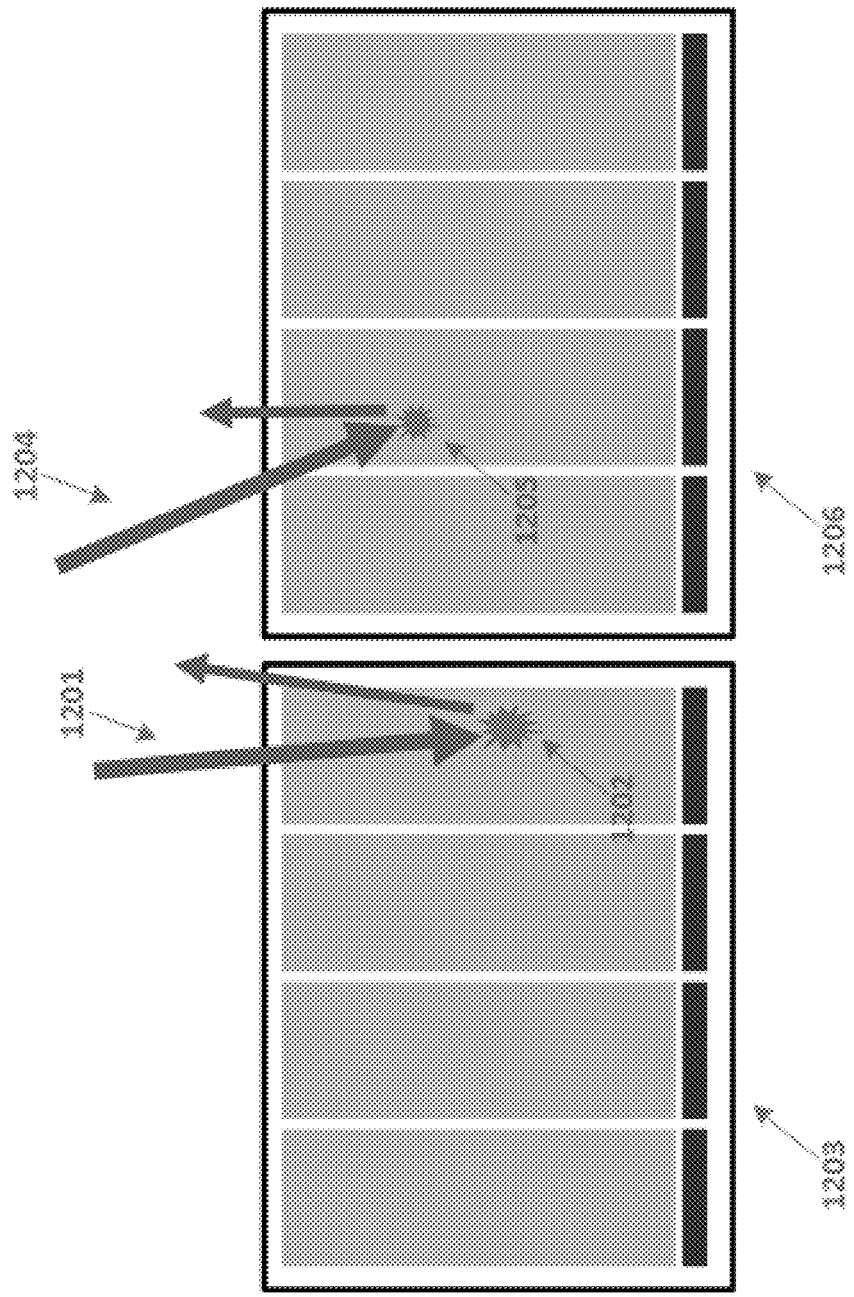
FIG. 12 illustrates a first example of a random assembly.
Figure 13:
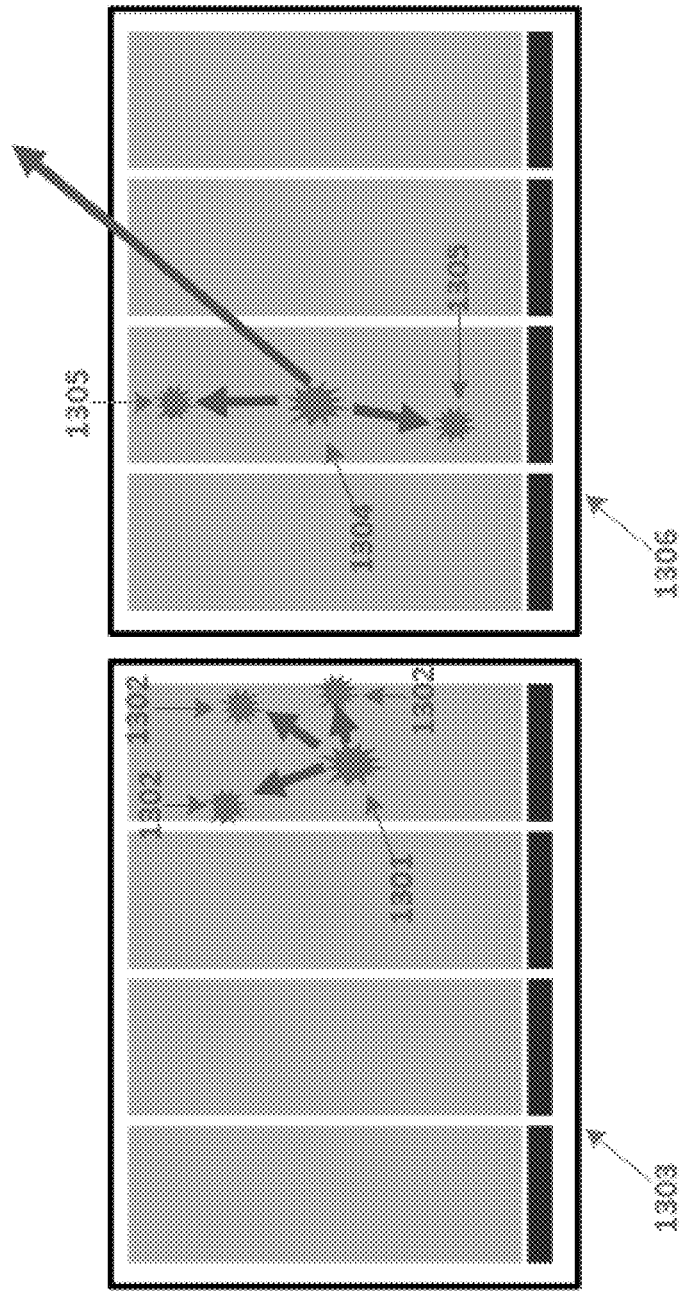
FIG. 13 illustrates a second example of a random assembly.

During the assembly process, and as introduced above, random assemblies will occur. A random assembly occurs when an event is assembled from hits which originated from two or more initiating events. FIG. 12 shows one example of a random assembly, where a first initiating event 1201 (e.g. a 511 keV incident gamma ray) causes a first hit 1202 within the first detector module 1203 and a second initiating event 1204 (e.g. a 511 keV incident gamma ray) causes a second hit 1205 within the second detector module 1206, both hits occurring within a same coincidence time window. As a result, the assembly process produces a random assembly event consisting of the first hit 1202 and a second hit 1205. FIG. 13 shows another example of a random assembly. In FIG. 13, a first initiating event 1301 (e.g. Lu-176 decay)

causes a first hit 1302 within the first detector module 1303, and a second initiating event 1304 (e.g. Lu-176 decay) causes a second hit 1305 in the second detector module 1306, both hits occurring within a same coincidence time window. Again, the assembly process may generate a random assembly event consisting of the first hit 1302 and the second hit 1305 even though they were caused by different initiating events.

One way to avoid significant contamination of data by random assemblies is to use a relatively low activity source. The number of random assemblies increases with the square of the activity. Lu-background is a good choice for scintillators in which it is present (such as LYSO, LSO, LGSO, etc.). The activity of Lu-background is low enough to prevent significant problems from random assemblies, yet it provides a high enough event rate so that enough data can be acquired in several seconds to a few minutes of acquisition time. Moreover, Lu-background is convenient because it is always present (i.e. no external source is required) and the half-life of Lu-176 is extremely long, making the Lu-background rate essentially constant over the life of a PET scanner.

In an embodiment, the region and/or sub-region made through geometric cuts in which assembly events are identified is referred to as the assembly region. The assembly region should be large enough (geometrically) to cover all of the defect-types that may be encountered. If there are no constraints on the type of defect that might be encountered, events can be assembled across the entire ring. If the source is a positron-emitter resulting in coincident back-to-back 511 keV gamma rays, geometric cuts should be made to the assembly region in order to eliminate a majority of the coincidences caused by separate 511 keV gamma rays so that hits from different 511 keV gamma rays are not assembled into a single event. Furthermore, limiting the assembly event region can reduce the contribution of random assemblies to noise and/or bias as there are fewer opportunities for random assemblies. Thus, one way to reduce the contribution of random assemblies to bias and noise is to limit the size of the assembly region that is used in the assembly process (e.g. the size of the assembly region should be only large enough to cover all desired defect-types). In other words, the assembly region only needs to be marginally larger than the largest deviation from the intended detector element arrangement error that needs to be detected. For instance, when detecting rotated modules, the assembly region only needs to be marginally larger than the diagonal length of one module As another example, when detecting swapped modules, the assembly region only needs to be marginally larger than the longest dimension of the module. In one exemplary embodiment, marginally larger can be the longest dimension or diagonal length of the detector element under inspection for arrangement errors rounded up to the nearest whole number of pixels (e.g. if the largest diagonal length of a module is 16.97 pixels, the assembly region has a radius of 17 pixels). Of course, it can be appreciated that marginally larger than the largest deviation can include other meanings, such increasing the longest dimension or diagonal length by a factor of 1-25%, or increasing the longest dimension or diagonal length by a fixed number of pixels, The selection of the geometric assembly range can often be chosen based on knowledge of the manufacturing or service process. Detector layout errors often result from defects that occur over a known distance range. For example, two neighboring modules might be swapped by incorrectly connecting cables, or multiple modules in a detector unit might be swapped by incorrect cabling. In these cases, the maximum extent of a defect sets a scale of approximately the longest dimension of a module or detector unit, respectively. In another example, two neighboring detector units might be swapped by incorrectly connecting cables. Swapping detector unit cables across a longer distance would be relatively easy to catch by visual inspection. In this case, the maximum extent of a defect sets a scale of approximately the longest dimension of a detector unit. In a third example, a module might be rotated by 90 or 180 degrees. In this case, the maximum extent of a defect sets a scale of approximately the longest diagonal dimension of a module. In a fourth example, a detector unit might be rotated by 180 degrees. In this case, the maximum extent of a defect sets a scale of approximately the longest diagonal dimension of a detector unit.

Figure 14A:
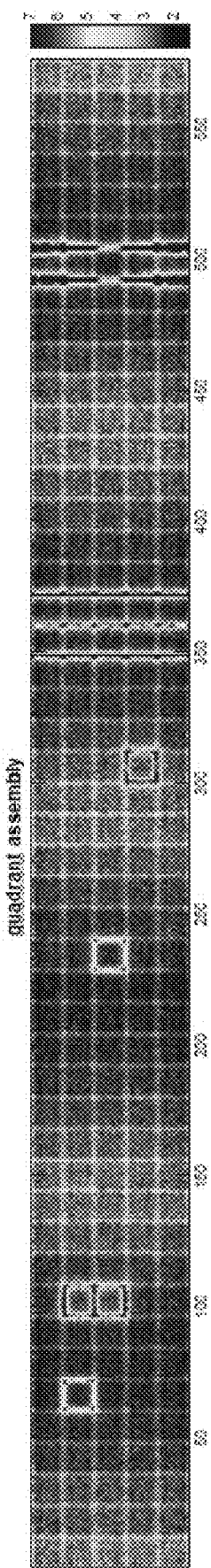
FIG. 14A shows an average distance map where the assembly region was fixed quadrants.
Figure 14B:
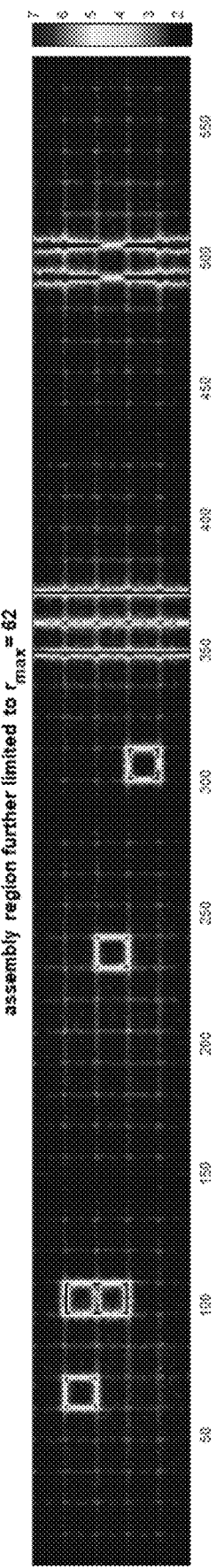
FIG. 14B shows an average distance map where the assembly region had size $r_{max}$=62 crystals.
Figure 14C:
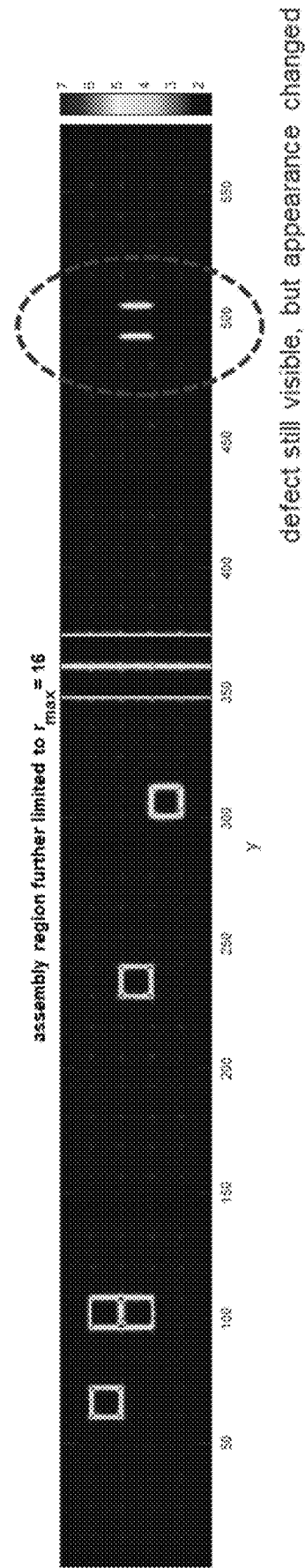
FIG. 14C an average distance map where the assembly region had size $r_{max}$=16 crystals.
Figure 15:
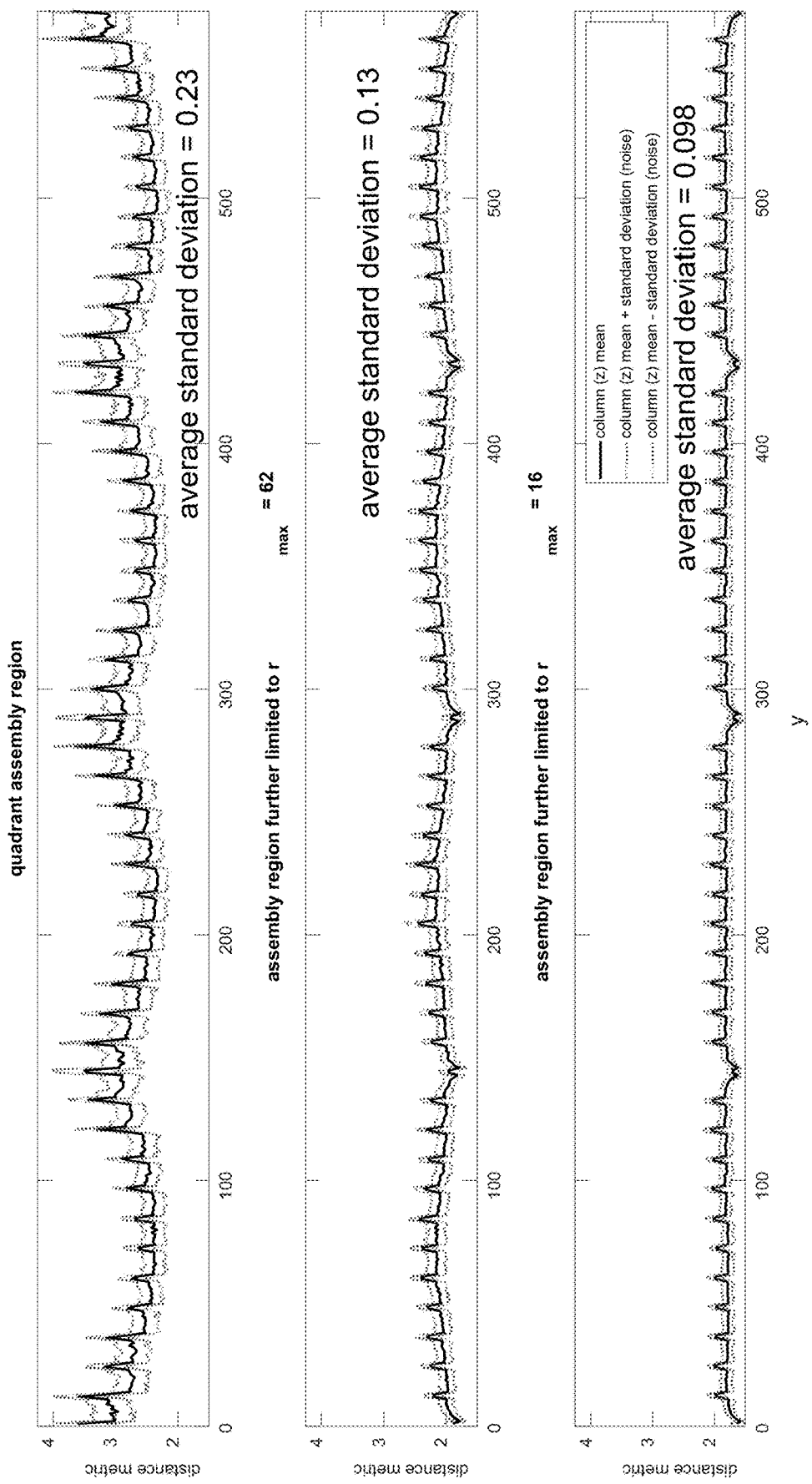
FIG. 15 shows the average distance and standard deviation value for each column making up a defect-free detector ring at different assembly region sizes.

To illustrate, FIG. 14A-14C show the results of reducing bias and noise by limiting the assembly region. The same defects from FIG. 11B are created and the unwrapped, two-dimensional view of the detector unit shown in each of FIG. 14A through FIG. 14C corresponds to the detector unit of FIG. 11A, wherein the detector units have a width of 12 pixels and length of 60 pixels and the modules have a width of 12 pixels and length of 12 pixels. In an embodiment, FIG. 14A demonstrates results when the assembly region is divided into quadrants, each one covering the entire axial extent and 12 modules/detector units in the trans-axial direction. Though the arrangement errors are still visible, as indicated by the noticeable outlines around the modules and detector units that are incorrectly placed, the correctly placed elements show some noise and bias, as indicated by the varying hues. In FIG. 14B, the assembly region is decreased to have a radius of 62 pixels (the approximate diagonal length of a detector unit is $\sqrt{12^2+60^2}=\sim61.2$ pixels, which can be rounded to 62). The defects are more discernable, as shown by the increased contrast between incorrectly and correctly placed detector elements. In FIG. 14C, the assembly region is further decreased to 18 pixels (the approximate diagonal length of a module is $\sqrt{12^2+12^2}=\sim16.97$, which is rounded up to 17). The defects are clearly visible, as shown by the strong contrast between incorrectly and correctly placed detector elements. As shown through FIG. 14A-14C, the noise and bias are observably lower as the assembly region is decreased. This can be further observed in FIG. 15 which includes a series of plots reflecting the effect of limiting the assembly region on bias and noise. For instance, the series of plots exhibit a mean distance and standard deviation along each column for a defect-free detector ring. The black curve is indicative of bias, and the gray-dashed envelope is indicative of noise. As illustrated in FIG. 15, as the assembly region decreased, the bias and noise decreased.

The bias from random assemblies can also be estimated and removed, thereby allowing the threshold level to be lowered. Recognizing that true and random assembly events contribute to the average distance map, the average distance map can be written as a weighted sum of two components, as follows:

$$d_i = \frac{T}{T+R}d\_true_i + \frac{R}{T+R}d\_rand_i \quad (1)$$

where $d_i$ is the average distance map, $d\_true_i$ is the contribution from true assemblies, $d\_rand_i$ is the contribution from random assemblies, the index i represents the pixel index in the map, T is the true assembly rate and R is the random assembly rate.

Furthermore, it can be written that:

$$R = \alpha T^2 (\Delta t) \quad (2)$$

where $\Delta t$ is the assembly coincidence window width and $\alpha$ is a proportionality constant (i.e. R is proportional to the square of the trues rate, T, and the coincidence window width, $\Delta t$). With this substitution, Equation (1) becomes:

$$d_i = \frac{d\_true_i}{1 + \alpha T(\Delta t)} + \frac{d\_rand_i}{1 + \frac{1}{\alpha T(\Delta t)}}. \quad (3)$$

According to an embodiment, if the data are acquired as a single hits list (i.e. event assembly is done off-line in a post-processing step), then the data from a single acquisition can be assembled with multiple values of $\Delta t$, where $\Delta t$ should be large enough so that all trues events are assembled. The value chosen for $\Delta t$ depends on the calibration state of the system. If timing channel offsets and energy-walk calibrations have not yet been performed, larger values of $\Delta t$ must be used to ensure that all trues assembly events are assembled. With an uncalibrated system, a $\Delta t$ in the range of 3-10 ns is often reasonable, though the choice depends on the details of the system. On a pixel-by-pixel basis, $[d_i(\Delta t)$ vs. $\Delta t]$ can be fit to Equation (3) to determine $d\_true_i$, $d\_rand_i$, and $\alpha T$. Note that if the event assembly is done in real-time, the same approach can be used, but multiple data sets must be acquired.

Figure 16A:
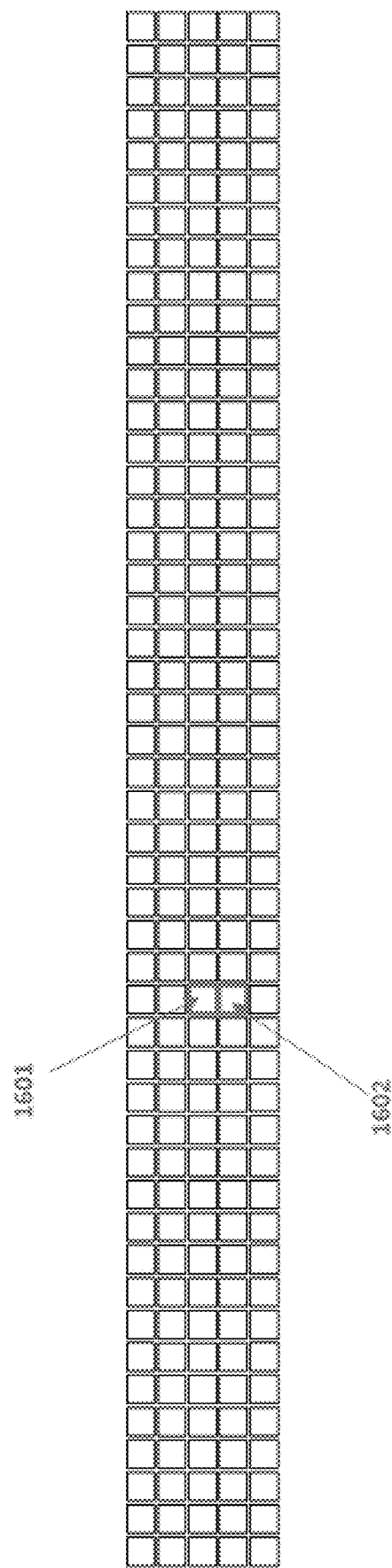
FIG. 16A illustrates an arrangement error where two modules are swapped.
Figure 16B:
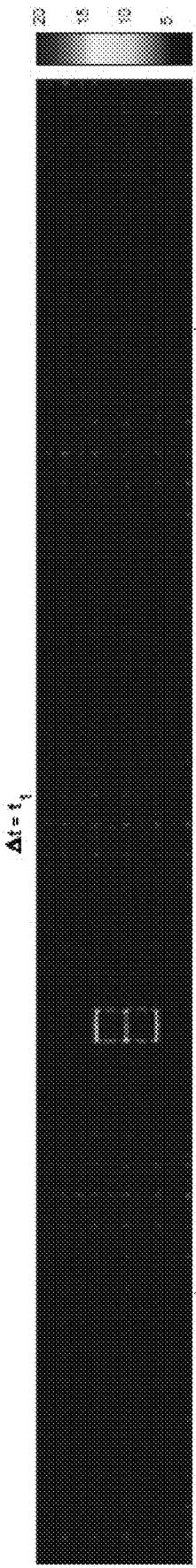
FIG. 16B illustrates an average distance map captured using a coincidence time window of one time constant ($\Delta t=t_1$)
Figure 16C:
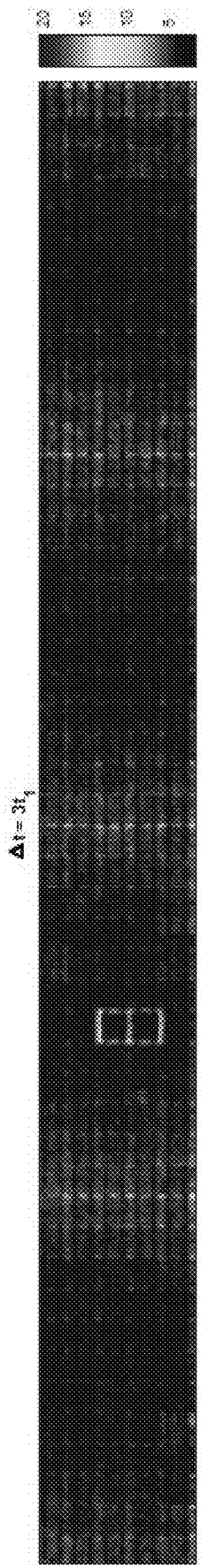
FIG. 16C illustrates an average distance map captured using a coincidence time window of three time constants ($\Delta t=3t_1$)
Figure 16D:
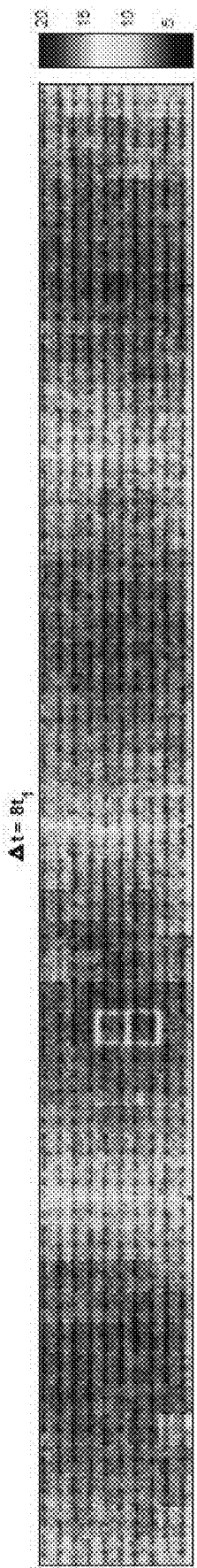
FIG. 16D illustrates an average distance map captured using a coincidence time window of eight time constants ($\Delta t=8t_1$)
Figure 16E:
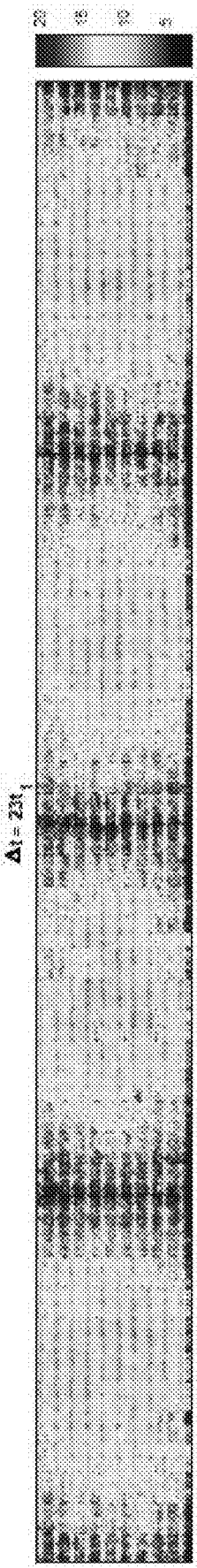
FIG. 16E illustrates an average distance map captured using a coincidence time window of 23 time constants ($\Delta t=23t_1$)
Figure 17A:
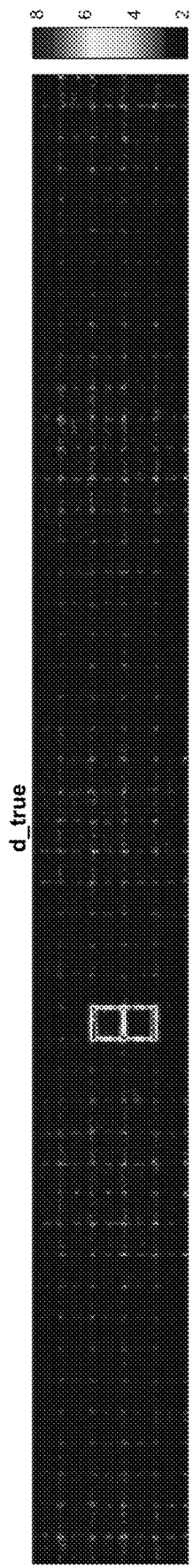
FIG. 17A shows an extracted true assembly events average distance map.
Figure 17B:
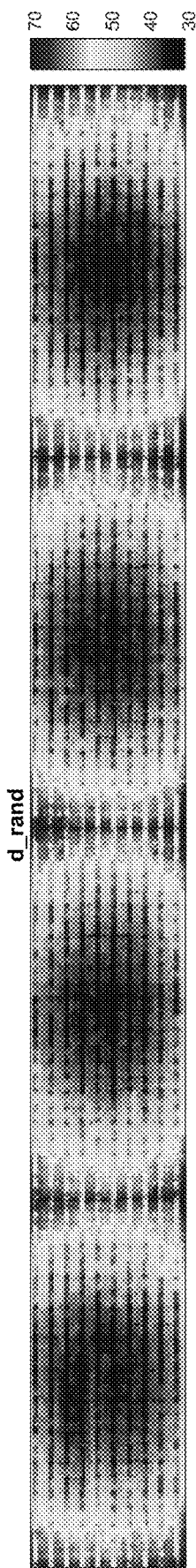
FIG. 17B shows a random assembly events average distance map.

According to an embodiment of the present disclosure, the above described approach will now be described. First, as shown in FIG. 16A, a data set may be acquired from a detector ring with a known defect, such as a case where a first module 1601 and a second module 1602 have been swapped. FIG. 16B-16E illustrates data processed to produce average distance maps using different coincidence windows $\Delta t$ from the detector described in FIG. 16A. In the example of FIG. 16B-16E, data was acquired using only Lu-background, which has a fairly low event initiation rate. The effect of random assemblies, of course, can be larger when external radiation sources are used. The captured data in FIG. 16B had a coincidence window of one time constant ($\Delta t = t_1$), the captured data in FIG. 16C had a coincidence window of three time constants ($\Delta t = 3t_1$), the captured data in FIG. 16D had a coincidence window of eight time constants ($\Delta t = 8t_1$), and the captured data in FIG. 16E had a coincidence window of 23 time constants ($\Delta t = 23t_1$). In FIG. 16B-16E, each average distance map reflects the crystal level. Similar techniques could be applied using other metrics or other levels, such as the module level or detector unit level. Also note that the assembly region of FIG. 16B-16E was divided into fixed quadrants. The data was then fit on a pixel-by-pixel basis to extract a true assemblies average distance map ($d\_true_i$), which is shown in FIG. 17A. The swapped modules are clearly visible, as indicated by the lighter perimeters of adjacent squares. An extracted random assemblies average distance map ($d\_rand_i$) is shown in FIG. 17B. The four repeats of the pattern arise from the use of four quadrants as the assembly region.

Figure 18:
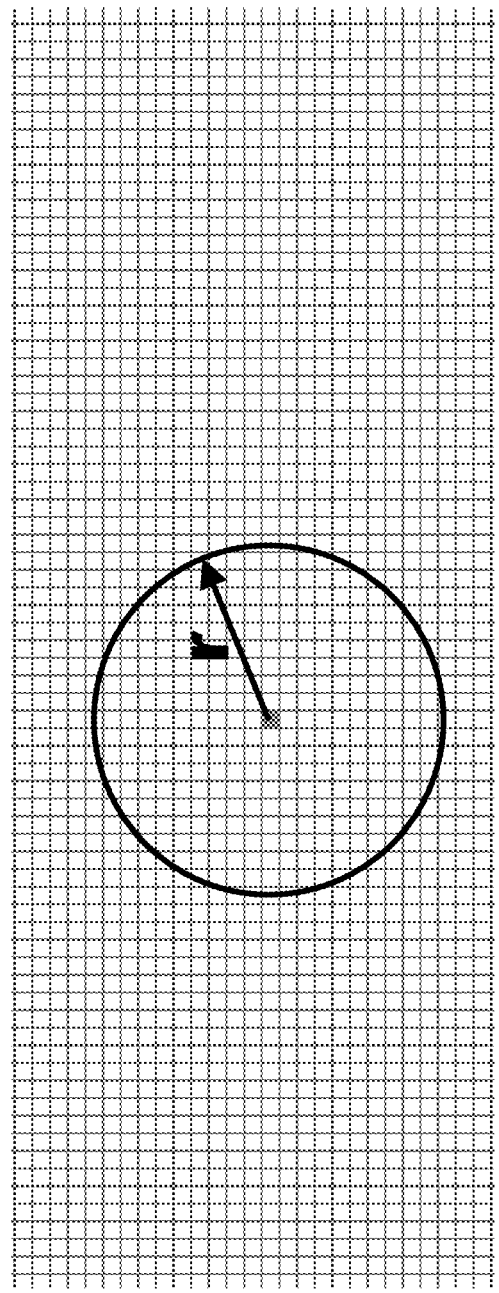
FIG. 18 shows an example of C(r) in an infinitely-large detector.
Figure 19:
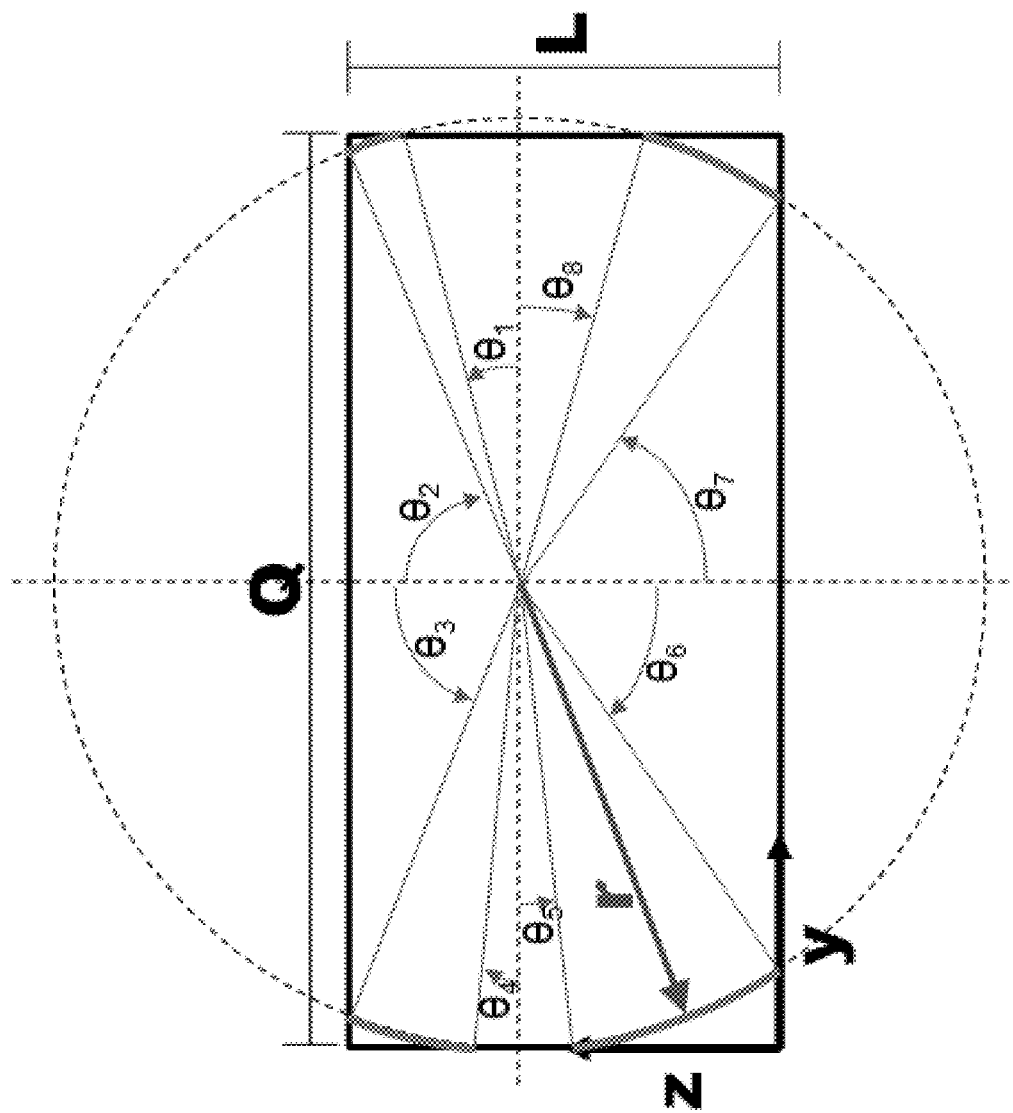
FIG. 19 shows an example of C(r) in a non-infinitely-large detector.

In an embodiment, the general pattern of the random assemblies average distance map ($d\_rand_i$) for each pixel i can also be pre-determined in order to avoid dependence on the experimental conditions and parameters (e.g. activity and $\Delta t$), using:

$$d\_rand_i = \frac{\int_1^{r_{max}} r \cdot C(r) \cdot dr}{\int_1^{r_{max}} C(r) \cdot dr} \quad (4)$$

where $d\_rand_i$ is an average distance due to random assembly events for pixel i, and $r_{max}$ is a maximum assembly radius (a parameter that depends on the chosen assembly process). The term in the denominator of Equation (4) is a normalization factor. $C(r)$ is the circumference of the circle with radius r that encloses all the pixels/crystals whose number of random assembly events need to be tracked. In an infinitely large detector, as represented in FIG. 18, the random assembly rate for a distance r would be proportional to $2\pi r$ because the random assembly rate varies with the distance r from the crystal of interest. In a non-infinitely large detector, only the portions of the circle which are within the assembly region contribute to the random assembly event rate. For example, referring to FIG. 19, $C(r)$ can be expressed as:

$$C(r) = (2\pi - \Sigma_{i=1}^8 \theta_i) r. \quad (5)$$

Furthermore, when fixed assembly regions are used, such as dividing into quadrants, the following equation may be used:

$$r_{max} = \max[r_{max1}, r_{max2}, r_{max3}, r_{max4}]. \quad (6)$$

Figure 20:
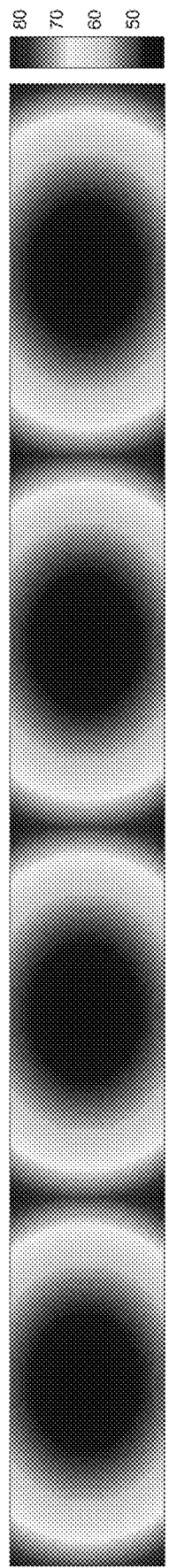
FIG. 20 shows an example of a random average distance map that was pre-calculated for fixed regions, where the sub-regions were quadrants.

An example of results from pre-calculating the random average map are shown in FIG. 20, wherein the fixed regions are the four quadrants of the detector ring. Note the similarities between FIG. 20 and FIG. 17B even though they were extracted using different methods. Also note the several symmetries which could be exploited to reduce the computational burden.

For a selected set of experimental conditions (e.g. isotope, activity, etc.), it can be written that:

$$d_i = \beta d\_true_i + (1-\beta) d\_rand_i \quad (7)$$

where a constant of proportionality ($\beta$) must be determined. The following will describe two methods to determine $\beta$, but other methods to determine $\beta$ may be possible. Both of the methods described herein determine a value of $\beta$ for a system (or systems) which is known to be defect-free. This value of $\beta$ can then be applied to all other systems.

One method for obtaining $\beta$ is by selecting the value of $\beta$ that minimizes variance, which will be referred to as Method A. For a selected set of experimental conditions (isotope, activity, etc.), it can written that:

$$d\_true\_est_i = \frac{d_i - (1-\beta) d\_rand_i}{\beta} \quad (8)$$

where $d\_true\_est_i$ is an estimated true average distance for a specific value of the constant of proportionality, $\beta$, $d\_true\_est_i$ is the map that is desired for defect detection because it excludes bias from random assemblies. At the outset of Method A, an average distance map, or $d_i$ (i is the pixel index), can be measured for a selected value of $\Delta t$. Then, based on a known-defect free system, $\beta$ can be varied and the variance of $d\_true\_est_i$ can be measured. The value of $\beta$ which results in the lowest value for the variance can then be selected.

Figure 21:
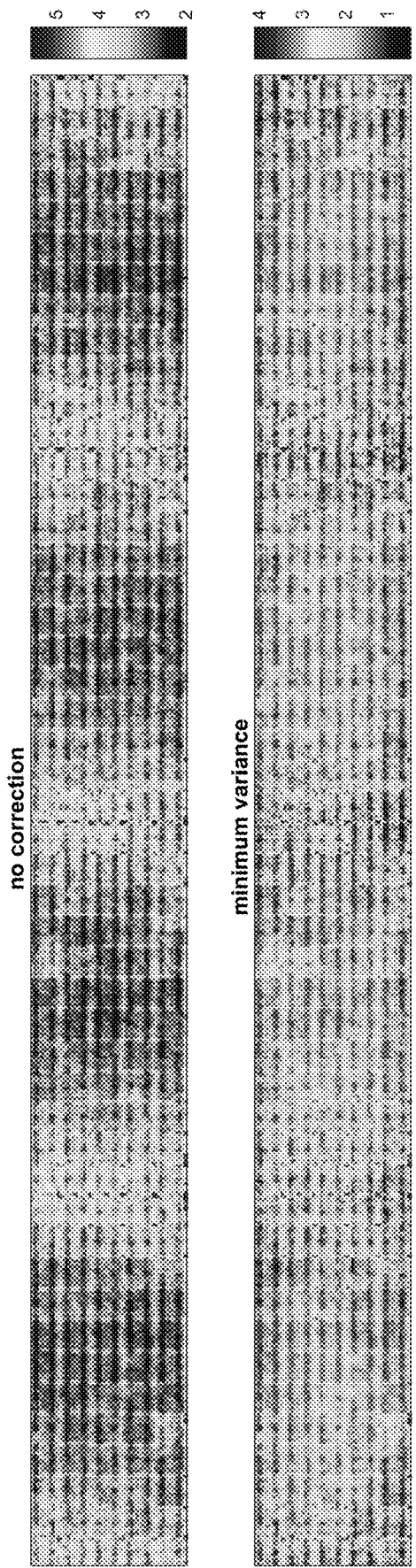
FIG. 21 shows average distance maps for a defect free system with no correction applied and one after Method A is applied.
Figure 22:
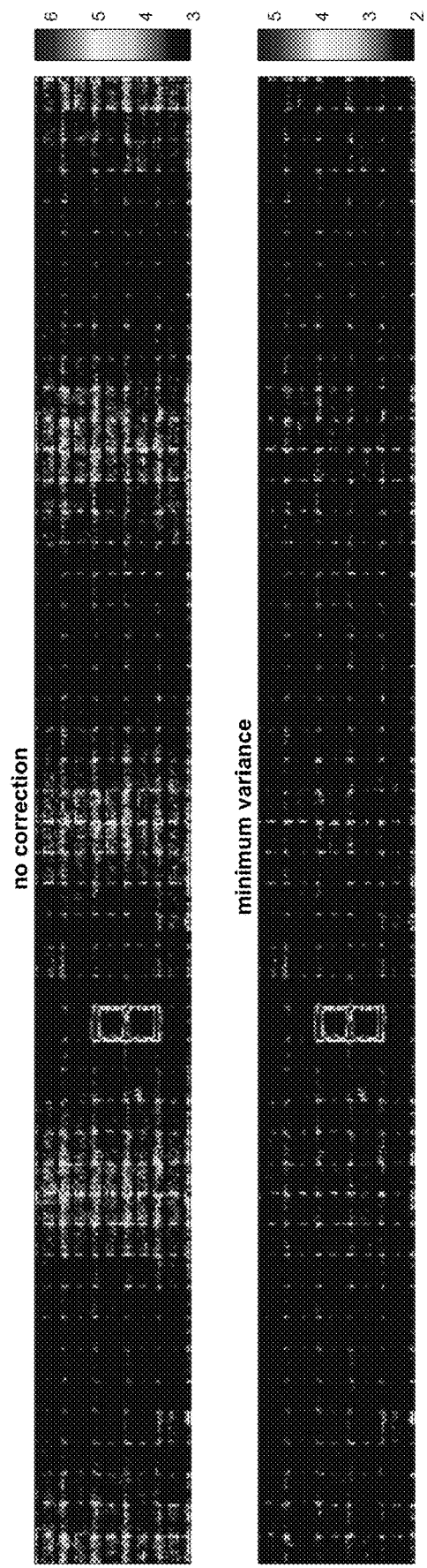
FIG. 22 shows average distance maps for a system that has swapped modules with no correction applied and one with Method A applied.

FIG. 21 shows an average distance map for a defect free system with no correction (top graph; labelled "no correction") and an estimated true average distance map using a value of β obtained using Method A (bottom graph; labelled "minimum variance"). Furthermore, FIG. 22 shows an average distance map for a system with swapped modules (same defects as in FIG. 16A) with no correction (top graph; labelled "no correction") and an estimated true average distance map using a value of β obtained using Method A (bottom graph; labelled "minimum variance"). Therefore, using β obtained using Method A allows the threshold for detecting defects to be set to a more sensitive value.

In a second method for obtaining β, which will be referred to hereinafter as Method B, it can be written that:

$$d_i = \beta_i d\_true_i + (1 - \beta_i) d_{rand_i} = \frac{T_i}{T_i + R_i} d\_true_i + \frac{R_i}{T_i + R_i} d\_rand_i \quad (9)$$

where $T_i$ is a true assembly rate and $R_i$ is a random assembly rate for pixel i. The prompt assembly rate, $P_i$, is a total rate in a pixel, $P_i = T_i + R_i$. This means:

$$\beta_i = \frac{P_i - R_i}{P_i}. \quad (10)$$

Since $P_i$ can be easily measured, the random assembly rate for each pixel, $R_i$, must be estimated in order to estimate $\beta_i$. Because $R_i$ is proportional to $\int_1^{r_{max}} C(r) \cdot dr$, it can be written that:

$$R_i = \gamma_i \int_1^{r_{max}} C(r) \cdot dr \quad (11)$$

where $\gamma_i$ is a proportionality constant. Next, it can be assumed that the majority of true assembly events involve hits which are in close proximity (for a defect free system). Therefore, a relatively large threshold radius, $r_{threshold}$, can be selected and known-defect-free data can be processed in order to only calculate $P_i(r > r_{threshold})$ (i.e. the prompt (total) rate for hits which have distances greater than $r_{threshold}$). This will be approximately equal to $R_i(r > r_{threshold})$ (i.e. the random assembly rate for hits which have distances greater than $r_{threshold}$):

$$R_i(r > r_{threshold}) \cong P_i(r > r_{threshold}) = \gamma_i \int_{r_{threshold}}^{r_{max}} C(r) \cdot dr \quad (12)$$

which can be re-arranged to arrive at:

$$\gamma_i \cong \frac{P_i(r > r_{threshold})}{\int_{r_{threshold}}^{r_{max}} C(r) \cdot dr}. \quad (13)$$

The random events assembly rate for all r can then be estimated using:

$$R_i = \gamma_i \int_1^{r_{max}} C(r) \cdot dr \quad (14)$$

and $$\beta_i = \frac{P_i - R_i}{P_i} \quad (14)$$

where $\beta_i$ can be calculated from obtained $P_i$ and $R_i$ values. The average of $\beta_i$ can be calculated and used as β to calculate d_true_est$_i$.

Figure 23:
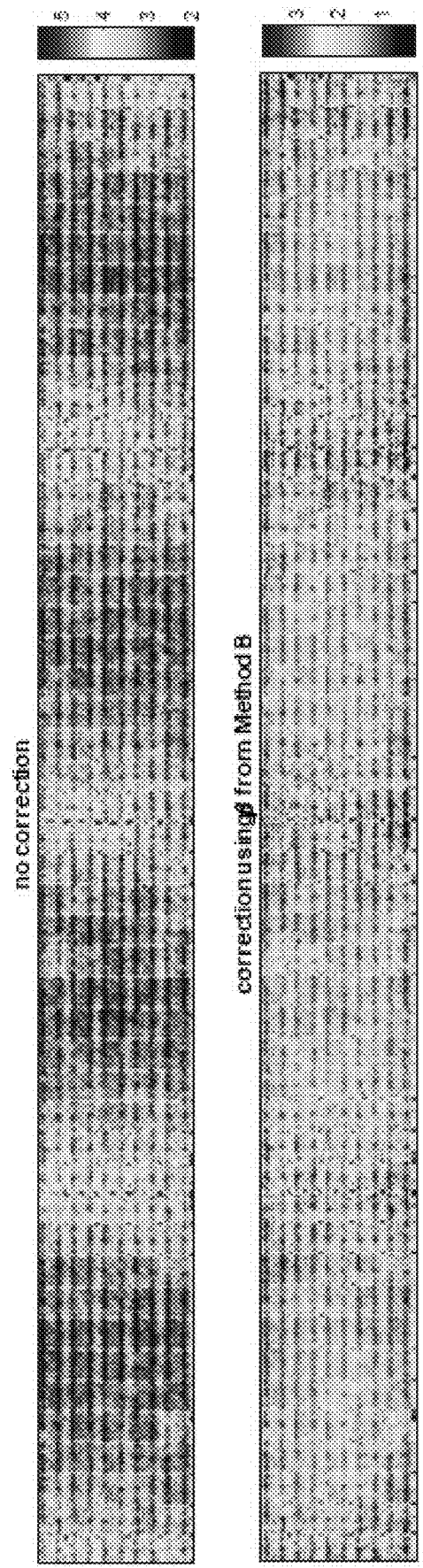
FIG. 23 shows average distance maps for a defect free system with no correction applied and one after Method B is applied.
Figure 24:
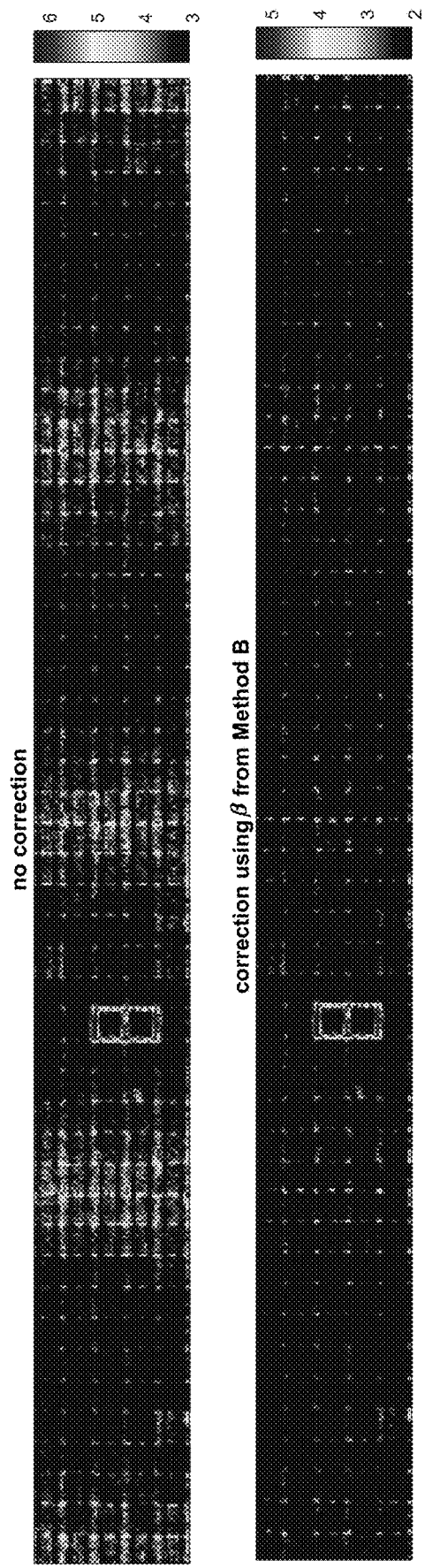
FIG. 24 shows average distance maps for a system that has swapped modules with no correction applied and one with Method B applied.

According to an embodiment, FIG. 23 shows average distance maps for a defect free system with no correction (top graph; labelled "no correction") and an estimated true average distance map using the value of β obtained from Method B (bottom graph; labelled "correction using β obtained from Method B") (used $r_{threshold}$=30 pixels)]. Furthermore, FIG. 24 shows average distance maps for a system with swapped modules (same defects as in FIG. 16A) that has no correction (top graph; labelled "no correction") and an estimated true average distance map for a system using the value of β obtained from Method B (bottom graph; labelled "correction using β from Method B"). By using the selection of β obtained from Method B, the threshold for detecting defects can be set to a more sensitive value.

Furthermore, if β is determined for one set of conditions (activity and Δt), a new value of β can be estimated for a different choice of activity and Δt. Assuming that $\beta_0$ is determined for activity Activity$_0$ and coincidence window $\Delta t_0$, a new value of $\beta_1$ for each pixel i can be calculated by substituting the following:

$$P_1 = \frac{Activity_1}{Activity_0} P_0 \quad (16)$$

$$R_1 = \frac{(Activity_1^2 \Delta t_1)}{(Activity_0^2 \Delta t_0)} R_o \quad (17)$$

into $$\beta_{1i} = \frac{P_{1i} - R_{1i}}{P_{1i}} \quad (18)$$

and re-calculating the average value of β to obtain $$\beta_i = \frac{P_i - R_i}{P_i}. \quad (19)$$

Figure 25:
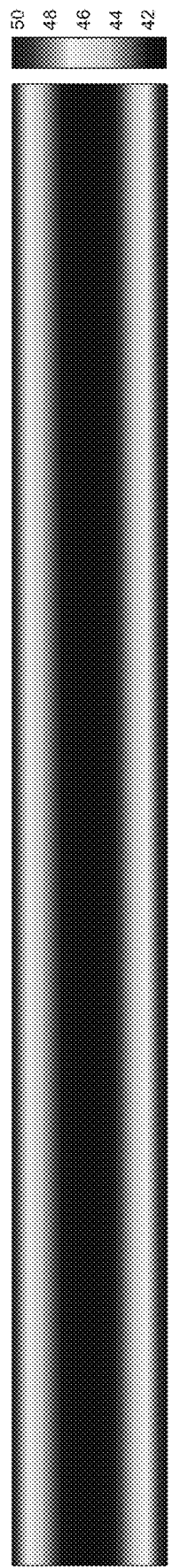
FIG. 25 shows an example of a random average map that was pre-calculated using centered-region geometric cuts.

According to an exemplary embodiment of the present disclosure, the preceding methods can also be applied to geometric cuts centered on the maximum energy hit. Referring back to FIG. 19, $$y = \frac{Q}{2}$$

can be used to calculate angles comprising C(r). FIG. 25 shows a result of a pre-calculated random assembly map using the preceding method for centered regions. Also note the several symmetries which could be exploited to reduce the computational burden.

In another exemplary embodiment, bias can be removed by acquiring uncorrected distance maps (i.e. no bias correction applied) from one or more known-defect-free systems. If multiple known-defect-free systems are available, their respective uncorrected distance maps can be averaged to create an average uncorrected distance map. In either case, distance maps acquired by the new system (i.e. system-under-test) not yet known to be defect-free can be corrected by normalizing its distance maps using a distance map resulting from a known-defect-free case. That is, the distance map can be divided by the known-defect-free map on an element-by-element basis to arrive at a corrected or normalized distance map. In another exemplary aspect, the distance map from the new system can be corrected by subtracting the known-defect-free distance map on an element-by-element basis. Either method produces corrected distance maps with very little bias.

Another way to deal with bias and its effect on the threshold level is to have a threshold level map (i.e. a threshold level which varies with position). The way the map varies in position is determined by bias. The threshold level map could be determined empirically or by calculating the bias level as described previously. As an example of the empirical method, the threshold level map could be determined by averaging results from several defect-free scanners and then increasing the threshold level by a multiple of the local standard deviation to prevent false positives.

Because defects are equivalent to a change in a LUT, defects can be corrected by using a different LUT, according to an exemplary embodiment of the present disclosure. Furthermore, real data can be used to create data with any conceivable defect. Many different defective datasets can be created, which lends itself to machine learning applications and could enable the ability to identify defects and determine how to correct them. The training data could be generated by creating defective LUTs, which are used to relate each detector element to its physical location.

Figure 26:
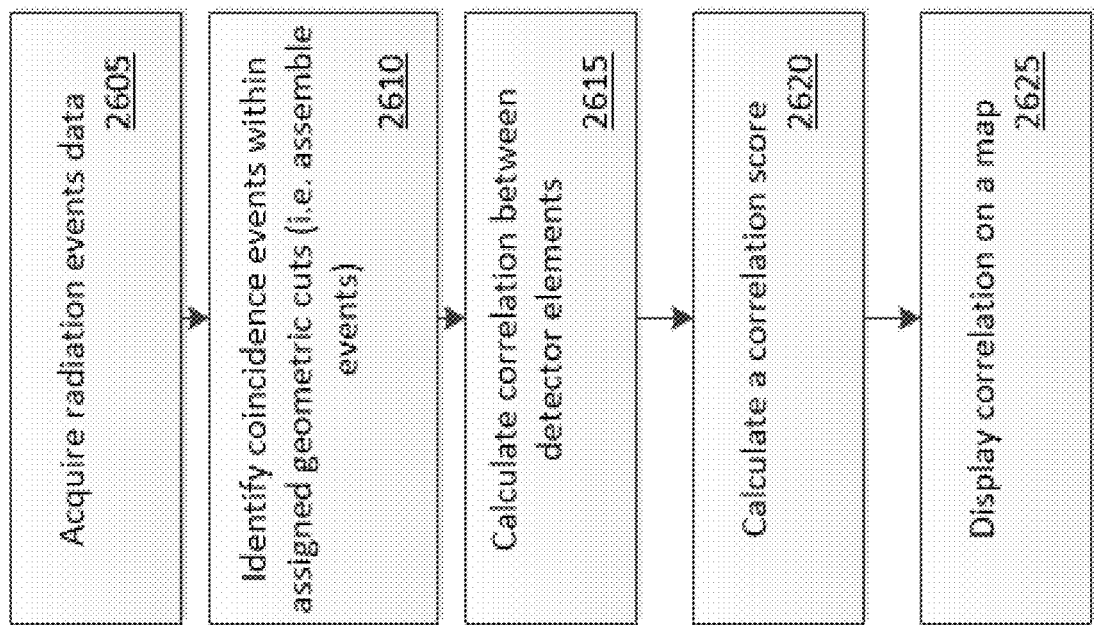
FIG. 26 is flowchart walking through another exemplary embodiment for detecting arrangement errors.

According to an exemplary embodiment of the present disclosure, and with reference now to the flow diagram of FIG. 26, a correlation metric can be used to measure the relative correlation of two detector elements. This method is similar to the previously-described embodiments, but differs in that a correlation score is used instead of a distance metric.

First, radiation events data can be acquired in step 2605. This includes coincidence events between detector elements using the crystal's natural multi-stage radiation background or with an external radiation source. The captured radiation events data can include position information (e.g. location of detector element where the hit occurred), time of hit occurring, and amount of energy deposited for each hit in the PET detector.

At step 2610, the acquired radiation events data can be used to identify coincidence events using an appropriately chosen geometric cut. Similar logic to that described above can be applied in choosing a geometric cut in this embodiment. Additionally, it is optional to process the coincidence events with time or energy calibration and further filter events with additional time or energy cuts.

Next, a relative correlation between detector elements can be determined at step 2615. Such a correlation should be normalized to minimize impact from variable efficiency of the detector, strength of background, and exposure to an external energy source. One way to define the correlation is to calculate a fraction of coincidence events among total number of events detected by two detectors, such as:

$$p(a, b) = \frac{N_{coincidence}(a, b)}{N_{singles}(a) + N_{singles}(b)} \quad (20)$$

where p(a, b) is a correlation between elements a and b, $N_{coincidence}(a, b)$ is a number of coincidence events shared between elements a and b, and $N_{singles}(a)$ and $N_{singles}(b)$ are a number of coincidence events detected by detector element a and b, respectively. The correlation between detector elements could be obtained at different levels, such as the crystal level, module level, or detector unit levels. Note that the correlation of combinations which are geometrically excluded is set to 0. Furthermore, it is optional to translate the correlation into other quantities to reduce uncertainty in positioning for better interpretation or to suppress statistical noise. One example is to convert the correlation value to an effective distance ($D_{Eff}$), where a strong correlation corresponds to a shorter $D_{Eff}$. The conversion could be done using a translation function ($D_{Eff}=D_{Eff}(P)$) or a LUT, for example.

Figure 27:
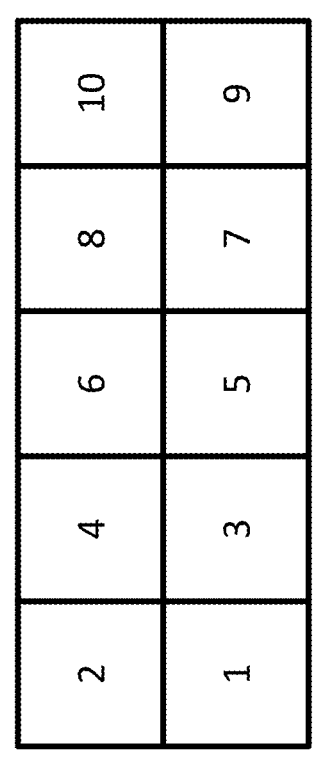

Next, the correlation (or effective distance) data could be converted into a correlation (or effective distance) score at step 2620. As an example, FIG. 27 illustrates a layout of 10 detector modules (each module numbered 1-10) that are arranged correctly. A correlation between all neighboring modules can be measured and calculated. This correlation is a module level correlation. As an example, for the layout shown in FIG. 27, the correlation score can be calculated using:

$$\begin{aligned}\text{Correlation Score} = \\ p(1, 2) + p(3, 4) + p(5, 6) + p(7, 8) + p(9, 10) + p(1, 3) + p(3, 5) + \\ p(5, 7) + p(7, 9) + p(2, 4) + p(4, 6) + p(6, 8) + p(8, 10)\end{aligned} \quad (21)$$

where the elements 1-10 were each paired with their closest neighboring elements.

Figure 28A:
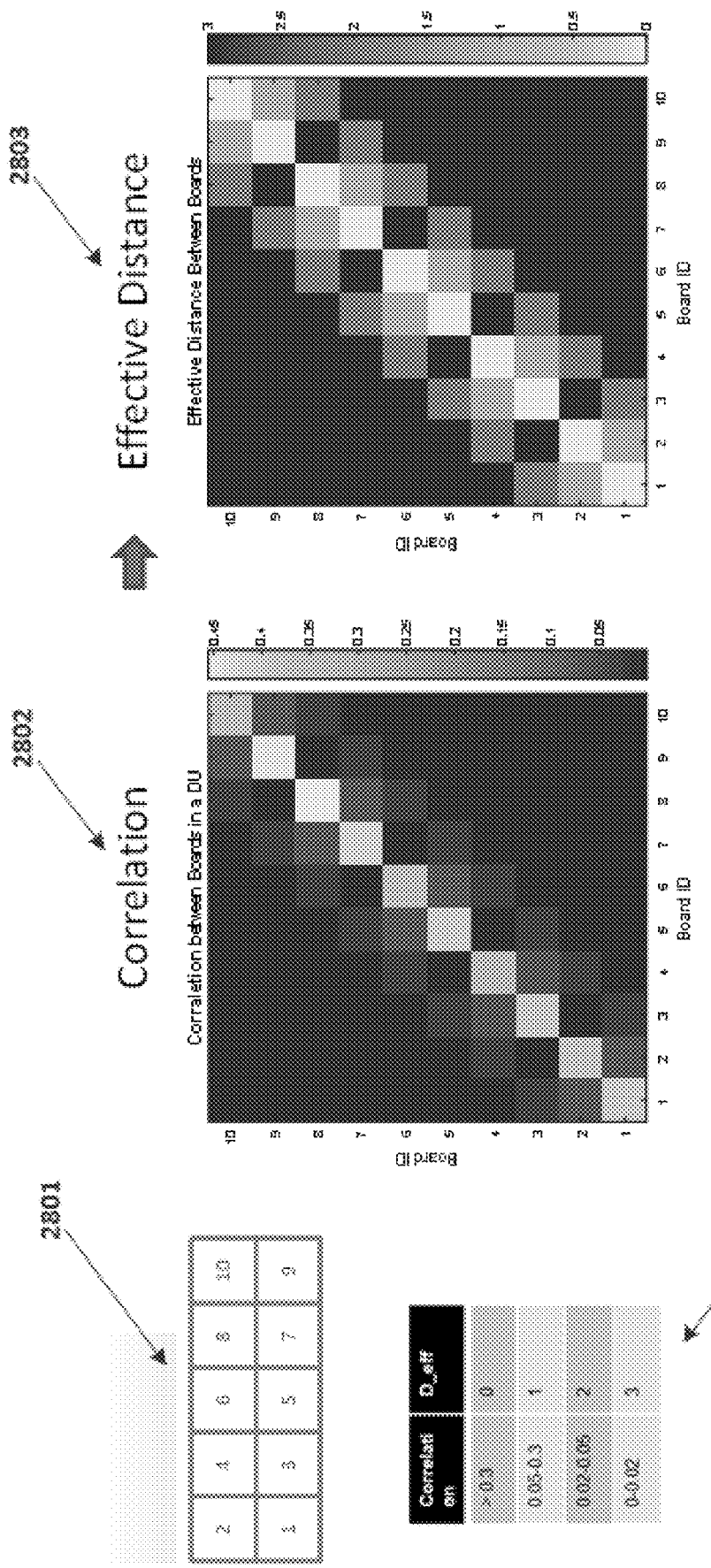
FIG. 28A shows the layout of a detector system (which is correct), the corresponding relative correlation map, an example of a way to convert relative correlation to an effective distance, and the resulting effective distance map.
Figure 28B:
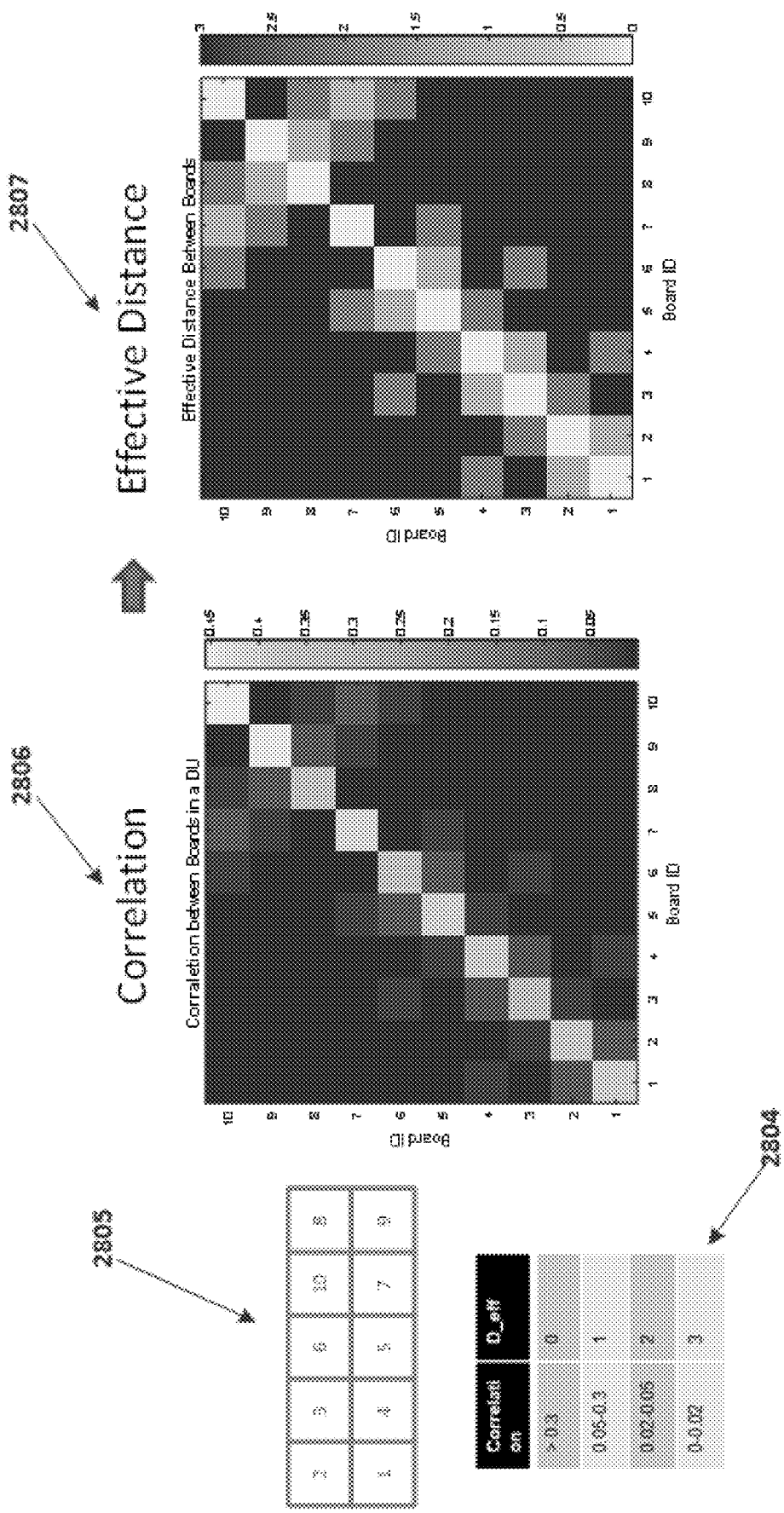
FIG. 28B shows an example of a way to convert relative correlation to an effective distance and the resulting effective distance map; and the layout of a detector system (which is incorrect), the corresponding relative correlation map, an example of a way to convert relative correlation to an effective distance, and the resulting effective distance map.

Referring back to FIG. 26, the correlation (or effective distance) between detector elements can be saved and displayed onto a map at step 2625. This allows for comparison of the map with a pre-defined template to identify layout errors. FIG. 28A shows an example of a layout 2801, comprised of 10 modules (i.e. boards), labeled 1-10 and correctly arranged. Correlation data can be acquired and displayed on a correlation map 2802. The correlation score for this map 2802 is 0.99. The correlation data can also be converted into an effective distance map 2803 using a conversion table 2804. The effective distance score for this map is 21. FIG. 28B shows an example of a layout 2805 where boards 8 and 10 have been incorrectly swapped. Correlation data can be acquired for this layout and displayed on a correlation map 2806. The correlation score for this map is 0.58. The correlation data can also be converted into an effective distance map 2807 using the table 2804. The effective distance score for this map is 30. These questionable correlation and effective distance scores help indicate the arrangement error.

When all the detector elements are positioned correctly, the correlations score should be the maximum value (correlation between elements is high). If an effective distance score is used, the effective distance should be the minimum value (distance between assembled events is low). A pre-defined threshold could be used against the overall score to judge whether the layout is correct or not. In the case no threshold can be applied, scores for all possible layout configurations can be calculated, and if the default configuration is not the extreme score (maximum for correlation score, minimum for effective distance) compared to the other configurations, a layout defect is likely to exist. Due to system symmetry, multiple configurations may all give extreme scores. In this case, the configuration which is most similar to the default configuration could be used as the correct one. Moreover, as was the case with previously-described embodiments, the correlation can be calculated at different levels (e.g. crystal level, module level, detector unit level).

Depending on manufacturing uniformity of a detector, some calibration of detectors may be needed. Detectors generally fall into two categories. The first category of detectors, which will be referred to as Category 1 detectors, are designed such that a signal from a scintillator crystal shared to multiple photosensors/electronics channels (i.e. scintillator pitch is not equal to photosensor pitch). The second category of detectors, which will be referred to as Category 2 detectors, minimize a signal shared from a scintillator crystal so that scintillator pitch is equal to photosensor pitch. Generally, Category 1 detectors require a position calibration to be performed before individual scintillator elements can be determined for hits. On the other hand, Category 2 detectors are able to identify the individual crystal of hits without any calibration. The methods described in this disclosure can work for Category 2 detectors, as well as Category 1 detectors that have been properly calibrated.

In view of the above, a full position calibration can be slow, and sometimes require manual checking and adjustment of segmentation results. However, for the purpose of this invention, a full position calibration of the Category 1 detector is not always required. To calculate distance maps or correlation metrics on a level lower than the module level, it is only required that spatial information within the module is available. Thus, a partial position calibration of Category 1 detectors could also be performed, which would allow the methods described in this disclosure to be implemented without requiring a full calibration process.

The following is an example of a method where a partial position calibration can be performed to achieve sufficient accuracy and produce distance maps or correlation metrics on a level lower than the module level. In this example, the module will be divided into nine regions of a 3×3 pattern. Generally, anything with more than 2×2 divisions will work, and the number of divisions in the X and Y directions does not need to be the same.

The first step is to start with a flood histogram (two dimensions). A flood histogram is typically made by flooding the detector with incident radiation, calculating locations (X,Y) for each detected event by Anger logic (which often contains significant spatial distortions), for example, and making a two-dimensional histogram of the locations (X, Y) of all the hits. Next, sum the histogram in the X-direction to collapse the flood histogram to one-dimension. Next, calculate the cumulative sum of the one-dimensional collapsed flood, then normalize the cumulative sum so that the final value of the cumulative sum is one (unity). Find the Y-values where the cumulative sum is closest to ⅓ and ⅔, which will be referred to as Y1 and Y2, respectively. Use these values of Y1 and Y2 as boundaries to define three horizontal regions, Region A, Region B and Region C. For each of these regions, from the flood histogram, sum in the Y-direction to collapse to one-dimension. For each region, calculate the cumulative sum of the one-dimensional collapsed flood, then normalize the cumulative sum so that the final value of the cumulative sum is one (unity). For each region, find the X-values where the cumulative sum is closest to ⅓ and ⅔. Call these values X1(R) and X2(R), respectively, where R represents the region label (A, B, C). Use these values of X1(R) and X2(R) as boundaries to define three regions within each of the original horizontal regions. These nine regions can be used as a sub-module region LUT, which is analogous to a crystal ID LUT, with an (X',Y') value assigned to each, or to generate X' and Y' LUTs. One of these types of LUTs (sub-module or combination of X' and Y') can then be used to assign an X' and Y' position to each hit (X,Y) for the purpose of calculating sub-module level distance maps or correlation metrics with Category 1 detectors.

Also note that PET systems generally require energy and timing offset calibration in order to achieve sufficient energy and timing resolution prior to clinical use. The techniques described in this disclosure enable a way to identify arrangement errors prior to calibration of the system. In one embodiment, a distance metric was used to aid in identifying arrangement errors. For multi-element detection events, distance metrics and time metrics can be related to each other based on the speed of light, since multi-element events require a gamma ray (either emitted or scattered at a first crystal) to travel the distance between the crystal elements involved in the multi-element event. It is important, however, to consider the effect of timing offset calibration. Timing offset calibration is required due to unavoidable manufacturing tolerances such as differences in cable lengths or timing response of different photosensors in the detectors, etc. Prior to calibration, timing offsets in a system can vary over a range of +/−1 ns or more, and the standard deviation of timing offsets is often in the range of several hundred picoseconds. Often, the arrangement errors that need to be detected are on the module level (e.g. swapped or rotated modules). Taking a typical lateral dimension of a module to be approximately 2 cm, and assuming that the gamma rays in multi-element events typically travel to neighboring modules, typical distances involved in the calculation will be on the order of 4 cm or less. With the speed of light being approximately $2.998 \times 10^{10}$ cm/sec, the typical distances correspond to approximately 130 ps or less of gamma ray time-of-flight. Since this value is a fraction of the typical offset values measured prior to timing offset calibration, the timing differences that would be measured for module-level arrangement errors prior to timing offset calibration would be difficult to correlate with distances because of the large timing offset errors.

In the preceding description, specific details have been set forth, such as a particular method and system for detecting arrangement errors of PET detectors. It should be understood, however, that techniques herein may be practiced in other embodiments that depart from these specific details, and that such details are for purposes of explanation and not limitation. Embodiments disclosed herein have been described with reference to the accompanying drawings. Similarly, for purposes of explanation, specific numbers, materials, and configurations have been set forth in order to provide a thorough understanding. Nevertheless, embodiments may be practiced without such specific details. Components having substantially the same functional constructions are denoted by like reference characters, and thus any redundant descriptions may be omitted.

Various techniques have been described as multiple discrete operations to assist in understanding the various embodiments. The order of description should not be construed as to imply that these operations are necessarily order dependent. Indeed, these operations need not be performed in the order of presentation. Operations described may be performed in a different order than the described embodiment. Various additional operations may be performed and/or described operations may be omitted in additional embodiments.

Those skilled in the art will also understand that there can be many variations made to the operations of the techniques explained above while still achieving the same objectives of the invention. Such variations are intended to be covered by the scope of this disclosure. As such, the foregoing descriptions of embodiments of the invention are not intended to be limiting. Rather, any limitations to embodiments of the invention are presented in the following claims.

Embodiments of the present disclosure may also be as set forth in the following parentheticals.

(1) A method for identifying arrangement errors of detector elements within a gamma-ray detector ring, the method comprising: acquiring detector element event data associated with radiation events within the detector elements of the gamma-ray detector ring; identifying, based on the detector element event data, assembly events between the detector elements of the gamma-ray detector ring; calculating a metric based on each of the assembly events between the detector elements of the gamma-ray detector ring; and identifying, based on the calculating, an arrangement error of the detector elements.

(2) The method of (1), wherein the detector element event data comprises a deposited energy of each of the radiation events, a time of energy deposition of each of the radiation events, and an energy deposition position of each of the radiation events.

(3) The method of any (1) or (2), wherein the assembly events between the detector elements are coincidence events that occur between two or more detector elements within geometrically-cut sub-regions of the gamma-ray detector ring.

(4) The method of any (1) to (3), wherein the detector element event data comprises a deposited energy of each of the radiation events and the geometrically-cut sub-regions for each of the assembly events are centered on a radiation event of the radiation events having a maximal deposited energy.

(5) The method of any (1) to (4), wherein the geometrically-cut sub-regions of the gamma-ray detector ring are marginally larger than a diagonal length of the detector elements.

(6) The method of any (1) to (5), wherein the geometrically-cut sub-regions of the gamma-ray detector ring are marginally larger than a longest dimension of the detector elements.

(7) The method of any (1) to (6), wherein the calculating calculates, as the metric, a distance metric defining a distance between assembly events for each detector element.

(8) The method of any (1) to (7), wherein the calculating calculates, as the metric, a relative correlation score between the detector elements.

(9) The method of any (1) to (8), further comprising: calculating the relative correlation score for all detector element layout combinations, identifying, based on the relative correlation score for all the detector element layout combinations, a correct detector element layout, and adjusting, based on the correct detector element layout, one or more look up tables used to relate each detector element to its physical location.

(10) The method of any (1) to (9), further comprising: collecting radiation events data at multiple time coincidence windows, identifying, based on the collecting, a contribution from random assembly events to the metric, and removing the contribution from random assembly events from the metric.

(11) The method of any (1) to (10), further comprising collecting radiation events data from a gamma-ray detector ring that is known to be defect-free, and removing, based on the collecting, a contribution from random assembly events from the metric of the gamma-ray detector ring.

(12) The method of any (1) to (11), further comprising: generating training data by creating defective look up tables used to relate each of the detector elements to its physical location, and training a machine learning system, using the training data, to identify arrangement errors.

(13) The method of any (1) to (12) further comprising: performing, prior to the acquiring, a partial position calibration when the gamma-ray detector ring is a Category 1 detector.

(14) The method of any (1) to (13), wherein the relative correlation score is a comparison between a number of coincidence events between a first detector element and a second detector element to a summation of a total number of radiation events in the first detector element and the second detector element.

(15) The method of any (1) to (14), wherein the detector elements are crystals.

(16) The method of any (1) to (15), wherein the detector elements are modules.

(17) The method of any (1) to (16), wherein the detector elements are detector units.

(18) A gamma-ray detector system for identifying arrangement errors of detector elements within a gamma-ray detector ring comprising: processing circuitry configured to acquire detector element event data associated with radiation events within the detector elements of the gamma-ray detector ring; identify based on the detector element event data, assembly events between the detector elements of the gamma-ray detector ring; calculate a metric based on the assembly events between the detector elements of the gamma-ray detector ring; and identify an arrangement error of the detector elements.

(19) The system of (18), wherein the processing circuitry is further configured to train a machine learning system based on training data generated by creating defective look up tables to identify an arrangement error.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

What is claimed is:

1. A method for identifying arrangement errors of detector elements within a gamma-ray detector ring, the method comprising:
   acquiring detector element event data associated with radiation events within the detector elements of the gamma-ray detector ring;
   identifying, based on the detector element event data, assembly events between the detector elements of the gamma-ray detector ring;
   calculating a metric based on each of the assembly events between the detector elements of the gamma-ray detector ring; and
   identifying, based on the calculating, an arrangement error of the detector elements.

2. The method of claim 1, wherein the detector element event data comprises a deposited energy of each of the radiation events, a time of energy deposition of each of the radiation events, and an energy deposition position of each of the radiation events.

3. The method of claim 1, wherein the assembly events between the detector elements are coincidence events that occur between two or more detector elements within geometrically-cut sub-regions of the gamma-ray detector ring.

4. The method of claim 3, wherein the detector element event data comprises a deposited energy of each of the radiation events and the geometrically-cut sub-regions for each of the assembly events are centered on a radiation event of the radiation events having a maximal deposited energy.

5. The method of claim 3, wherein the geometrically-cut sub-regions of the gamma-ray detector ring are marginally larger than a diagonal length of the detector elements.

6. The method of claim 3, wherein the geometrically-cut sub-regions of the gamma-ray detector ring are marginally larger than a longest dimension of the detector elements.

7. The method of claim 1, wherein the calculating calculates, as the metric, a distance metric defining a distance between assembly events for each detector element.

8. The method of claim 1, wherein the calculating calculates, as the metric, a relative correlation score between the detector elements.

9. The method of claim 8, further comprising:
calculating the relative correlation score for all detector element layout combinations,
identifying, based on the relative correlation score for all the detector element layout combinations, a correct detector element layout, and
adjusting, based on the correct detector element layout, one or more look up tables used to relate each detector element to its physical location.

10. The method of claim 1, further comprising:
collecting radiation events data at multiple time coincidence windows,
identifying, based on the collecting, a contribution from random assembly events to the metric, and
removing the contribution from random assembly events from the metric.

11. The method of claim 1, further comprising
collecting radiation events data from a gamma-ray detector ring that is known to be defect-free, and
removing, based on the collecting, a contribution from random assembly events from the metric of the gamma-ray detector ring.

12. The method of claim 1, further comprising:
generating training data by creating defective look up tables used to relate each of the detector elements to its physical location, and
training a machine learning system, using the training data, to identify arrangement errors.

13. The method of claim 1, further comprising:
performing, prior to the acquiring, a partial position calibration when the gamma-ray detector ring is a Category 1 detector.

14. The method of claim 8, wherein the relative correlation score is a comparison between a number of coincidence events between a first detector element and a second detector element to a summation of a total number of radiation events in the first detector element and the second detector element.

15. The method of claim 1, wherein the detector elements are crystals.

16. The method of claim 1, wherein the detector elements are modules.

17. The method of claim 1, wherein the detector elements are detector units.

18. A gamma-ray detector system for identifying arrangement errors of detector elements within a gamma-ray detector ring comprising:
processing circuitry configured to
acquire detector element event data associated with radiation events within the detector elements of the gamma-ray detector ring;
identify based on the detector element event data, assembly events between the detector elements of the gamma-ray detector ring;
calculate a metric based on the assembly events between the detector elements of the gamma-ray detector ring; and
identify an arrangement error of the detector elements.

19. The gamma-ray detector system of claim 18, wherein the processing circuitry is further configured to train a machine learning system based on training data generated by creating defective look up tables to identify an arrangement error.

* * * * *